United States Patent
Wasan

(10) Patent No.: US 10,543,202 B2
(45) Date of Patent: Jan. 28, 2020

(54) TOPICAL NIFEDIPINE FORMULATIONS AND USES THEREOF

(71) Applicant: University of Saskatchewan, Saskatoon (CA)

(72) Inventor: Ellen K. Wasan, Saskatoon (CA)

(73) Assignee: UNIVERSITY OF SASKTACHEWAN, Saskatoon (CA)

( * ) Notice: Subject to any disclaimer, the term of this patent is extended or adjusted under 35 U.S.C. 154(b) by 0 days.

(21) Appl. No.: 15/987,505

(22) Filed: May 23, 2018

(65) Prior Publication Data
US 2018/0344714 A1    Dec. 6, 2018

Related U.S. Application Data

(60) Provisional application No. 62/512,431, filed on May 30, 2017.

(30) Foreign Application Priority Data

May 30, 2017    (CA) ..................................... 2968861

(51) Int. Cl.

| | |
|---|---|
| A61K 31/4422 | (2006.01) |
| A61K 47/10 | (2017.01) |
| A61K 47/20 | (2006.01) |
| A61K 47/44 | (2017.01) |
| A61K 9/00 | (2006.01) |
| A61K 9/107 | (2006.01) |
| A61P 17/02 | (2006.01) |
| A61K 9/06 | (2006.01) |
| A61K 31/12 | (2006.01) |
| A61K 31/352 | (2006.01) |

(52) U.S. Cl.
CPC ........ *A61K 31/4422* (2013.01); *A61K 9/0014* (2013.01); *A61K 9/06* (2013.01); *A61K 9/107* (2013.01); *A61K 47/10* (2013.01); *A61K 47/20* (2013.01); *A61K 47/44* (2013.01); *A61P 17/02* (2018.01); *A61K 31/12* (2013.01); *A61K 31/352* (2013.01); *A61K 2300/00* (2013.01)

(58) Field of Classification Search
CPC .... A61K 31/522; A61K 31/4422; A61P 17/00
See application file for complete search history.

(56) References Cited

U.S. PATENT DOCUMENTS

| | | | |
|---|---|---|---|
| 4,904,699 A | 2/1990 | Bauer | |
| 8,663,663 B1 | 3/2014 | Ray, II | |

FOREIGN PATENT DOCUMENTS

| | | | |
|---|---|---|---|
| CA | 2047482 A1 | 1/1992 | |
| IT | 1209298 B | 7/1989 | |
| WO | 9102497 A1 | 3/1991 | |
| WO | WO9102497 | * | 3/1991 |
| WO | 0249603 A1 | 6/2002 | |

OTHER PUBLICATIONS

Landry's publication, J Vasc Surg, 2013, 57:1710-6.*
Mohammed et al. Improving the photostability of nifedipine in a topical emulsion formulation for use in Raynaud's Syndrome, 2015.*
Hayase et al., Journal od Pharmaceutical Sciences, 1994, 83(4):532-8.*
Gomathi et al., Biomaterials, 2003, 24:2767-2772.*
Choquenet et al., J. Nat. Prod., 2008, 71: 117-1118.*
Kockler et al., Profiles of Drug Substances Excipients, and Related Methodology, 2013, vol. 38, Chapter 3, pp. 87-93.*
Wasan, EK "Development of a topical nifedipine formulation for the treatment of raynaud's disease and chilblains." Applied Research Day, British Columbia Institute of Technology (oral presentation), Burnaby, BC, May 2013.
Mohammed M, Syeda J, Poteet J, Mitchell D, Krol E, Gosh S, Cawthray J, Wasan EK. "Topical nifedipine for the treatment of Raynaud's Syndrome." Abstract #72. Canadian Society for Pharmaceutical Sciences Annual Symposium. J Pharm Pharm Sci vol. 19(3) s105. May 2016.
Wasan, EK, "Topical Nifedipine for the Treatment of Raynaud Phenomenon". Department of Rheumatology Grand Rounds oral presentation. Royal University Hospital, Saskatoon, SK, Canada. Nov. 14, 2016.
Ennis, H., et al., "Calcium channel blockers for primary Raynaud's phenomenon". Cochrane Database Syst Rev, 2014, Issue 1, Art. No. CD002069.
Landry, G.J., "Current medical and surgical management of Raynaud's syndrome". J Vasc Surg, 2013, 57(6): pp. 1710-1716.
Ennis, H., et al., "Calcium channel blockers for primary Raynaud's phenomenon". Cochrane Database Syst Rev, 2016, Issue 2, Art. No. CD002069.
Chung, L., et al., "MQX-503, a novel formulation of nitroglycerin, improves the severity of Raynaud's phenomenon: a randomized, controlled trial". Arthritis Rheum, 2009. 60(3): p. 870-7.
McClusky S.V., et al., "Nifedipine in Compounded Oral and Topical Preparations". International Journal of Pharmaceutical Compounding, 2011. 15(2): p. 166-169.
Hayase, N., et al., "Newly discovered photodegradation products of nifedipine in hospital prescriptions". J Pharm Sci, 1994. 83(4), p. 532-8.
Aman, W. et al., "Particular features of photolabile substances in tablets". Pharmazie, 2003. 58(9): p. 645-50.
Goerner, H., "Nitro group photoreduction of 4-(2-nitrophenyl)- and 4-(3-nitrophenyl)-1,4-dihydropyridines". Chemical Physics, 2010. 373(3): p. 153-158.
Grooff, D., et al., "Photostability of crystalline versus amorphous nifedipine and nimodipine". J Pharm Sci, 2013. 102(6): p. 1883-94.

(Continued)

*Primary Examiner* — Rei Tsang Shiao
(74) *Attorney, Agent, or Firm* — Bereskin & Parr LLP/S.E.N.C.R.L., S.R.L.; Patricia Folkins

(57) ABSTRACT

The present application relates to topical formulations in the form of an oil-in-water emulsion comprising nifedipine and a photostabilizing effective amount of quercetin or a photostabilizing effective amount of a combination of quercetin and butyl methoxydibenzoylmethane (BMDBM). Such topical formulations may, for example, be used for the treatment of diseases, disorders or conditions that benefit from topical administration of nifedipine such as but not limited to Raynaud phenomenon, chilblains or wound healing.

20 Claims, 12 Drawing Sheets

(56) References Cited

OTHER PUBLICATIONS

Chaiprasongsuk, A., et al., "Photoprotection by dietary phenolics against melanogenesis induced by UVA through Nrf2-dependent antioxidant responses". Redox Biol, 2016. 8: p. 79-90.

Choquenet, B., et al., "Quercetin and rutin as potential sunscreen agents: determination of efficacy by an in vitro method". J Nat Prod, 2008. 71(6): p. 1117-8.

Kockler, J., et al., Chapter Three—Butyl Methoxy Dibenzoylmethane, in Profiles of Drug Substances, Excipients and Related Methodology, G.B. Harry, Editor. 2013, Academic Press. p. 87-111.

Doersch, K.M. et al., "The impact of quercetin on wound healing relates to changes in αV and β1 integrin expression" Exp Biol Med, Aug. 2017; 242(14): p. 1424-1431. Epub May 26, 2017.

Hatahet, T. et al., "Quercetin topical application, from conventional dosage forms to nanodosage forms." Eur J Pharm Biopharm 2016, 108: 41-53.

Grey, J.E. et al., "Venous and arterial leg ulcers". BMJ : British Medical Journal. 2006;332(7537):347-350.

Fasani, E. et al., "Photochemistry of 4-(2-Nitrophenyl)-1,4-Dihydropyridines. Evidence for Electron Transfer and Formation of an Intermediate". Photochem Photobiol 2006, 82(1), 225-230.

Afonso, S., et al., "Photodegradation of avobenzone: stabilization effect of antioxidants". J Photochem Photobiol B, 2014. 140: p. 36-40.

Gaspar, et al., "Photostability and efficacy studies of topical formulations containing UV-filters combination and vitamins A, C and E". Int J Pharm, 2007. 343(1-2): p. 181-9.

Golfram, F., et al., "The effect of topical nifedipine in treatment of chronic anal fissure". Acta Med Iran, 2010. 48(5): p. 295-9.

Agrawal, V., et al., "Randomized controlled pilot trial of nifedipine as oral therapy vs. topical application in the treatment of fissure-in-ano". Am J Surg, 2013. 206(5): p. 748-51.

Ashkani-Esfahani, S., et al., "Verapamil, a Calcium-Channel Blocker, Improves the Wound Healing Process in Rats with Excisional Full-Thickness Skin Wounds Based on Stereological Parameters". Adv Skin Wound Care, 2016. 29(8): p. 271-4.

Pai, D.R. et al., "Techniques in Chronic Wound Management: Review of the Literature and Recent Concepts". Journal of Novel Physiotherapies, 2013. 3: p. 2.

Torsiello, M.J. et al., "Transdermal nifedipine for wound healing: case reports". International Journal of Pharmaceutical Compounding, 2000. 4(5): p. 356-358.

Golfam, F., et al., "Comparison of topical nifedipine with oral nifedipine for treatment of anal fissure: a randomized controlled trial". Iran Red Crescent Med J, 2014. 16(8): p. e13592.

Bhaskar, H.N., et al., "Effect of nifedipine and amlodipine on dead space wound healing in rats". Indian J Exp Biol, 2005. 43(3): p. 294-6.

Bhaskar, K., et al., "Development of nitrendipine controlled release formulations based on SLN and NLC for topical delivery: in vitro and ex vivo characterization". Drug Dev Ind Pharm, 2008. 34(7): p. 719-25.

Bagheri, M., et al., "Azelnidipine, a new calcium channel blocker, promotes skin wound healing in diabetic rats". J Surg Res, 2011. 169(1): p. e101-7.

Yang, S.Y., et al., "A Comparison of Gene Expression of Decorin and MMP13 in Hypertrophic Scars Treated With Calcium Channel Blocker, Steroid, and Interferon: A Human-Scar-Carrying Animal Model Study". Dermatol Surg, 2017. 43 Suppl 1: p. S37-s46.

Vedakumari, W.S., et al., "Quercetin impregnated chitosan-fibrin composite scaffolds as potential wound dressing materials—Fabrication, characterization and in vivo analysis". Eur J Pharm Sci. Jan. 15, 2017;97:106-112. doi: 10.1016/j.ejps.2016.11.012. Epub Nov. 15, 2016.

Woo, T.Y., et al., "Nifedipine in scleroderma ulcerations". Int J Dermatol. 1984, 23(10):678-80.

Seo, S.H., et al., "*Polygonum aviculare* L. and its active compounds, quercitrin hydrate, caffeic acid, and rutin, activate the Wnt/β-catenin pathway and induce cutaneous wound healing". Phytother Res. May 2016;30(5):848-54. doi: 10.1002/ptr.5593. Epub Mar. 1, 2016.

Wu, S.C., et al., "Foot ulcers in the diabetic patient, prevention and treatment". Vasc Health Risk Manag, 2007. 3(1): p. 65-76.

Singh, N., et al., "Preventing foot ulcers in patients with diabetes". JAMA, 2005. 293(2): p. 217-28.

Canadian Institute for Health Information, "Compromised wounds in Canada" Aug. 2013, https://secure.cihi.ca/free_products/AiB_Compromised_Wounds_EN.pdf.

Tom, W., "Case Report: Wound Care of a Diabetic Foot Ulcer". International Journal of Pharmaceutical Compounding, Jul. 2004: p. 265.

Grossman, J.A., et al., "Successful combined medical and surgical treatment of a lower extremity sclerodermal ulcer". Ann Plast Surg. 1988, 20(6):582-585.

Castangia, I., et al., "Fabrication of quercetin and curcumin bionanovesicles for the prevention and rapid regeneration of full-thickness skin defects on mice". Acta Biomater. 2014, 10(3):1292-300. doi: 10.1016/j.actbio.2013.11.005. Epub Nov. 15, 2013.

Dinda, M., et al., "The water fraction of Calendula officinalis hydroethanol extract stimulates in vitro and in vivo proliferation of dermal fibroblasts in wound healing" Phytother Res Oct. 2016;30(10): p. 1696-1707 Epub Jul. 18, 2016.

Forte, L., et al., "Antioxidant and bone repair properties of quercetin-functionalized hydroxyapatite: An in vitro osteoblast-osteoclast-endothelial cell co-culture study". Acta Biomater Mar. 1, 2016; 32:298-308, Epub Dec. 12, 2015.

Yuan, Z., et al., "Quercetin inhibits the migration and proliferation of astrocytes in wound healing". Neuroreport May 6, 2015; 26(7):387-93.

Jangde, R., et al., "Preparation and optimization of quercetin-loaded liposomes for wound healing, using response surface methodology". Artif Cells Nanomed Biotechnol. 2016; 44(2):635-41, Epub Nov. 6, 2014.

Gomathi, K., et al., "Quercetin incorporated collagen matrices for dermal wound healing processes in rat". Biomaterials Jul. 2003; 24(16): 2767-72.

Meyrick Thomas, R.H., et al., "Nifedipine in the treatment of Raynaud's phenomenon in patients with systemic sclerosis" Br J Dermatol Aug. 1987; 117(2):237-41.

Rirash, F. et al., "Calcium channel blockers for primary and secondary Raynaud's phenomenon" Cochrane Database Syst Rev. Dec. 13, 2017;12:CD000467.

Winston, E.L. et al., "Nifedipine as a therapeutic modality for Raynaud's phenomenon" Arthritis Rheum Oct. 1983; 26(10): 1177-80.

Kahan, A., et al. "Nifedipine in digital ulceration in scleroderma" Arthritis Rheum Jun. 1983; 26(6): 809.

Jaffe, I.A., et al. "Nifedipine in digital ulceration in scleroderma" Arthritis Rheum Oct. 1982; 25(10): 1267-9.

\* cited by examiner

TOPICAL NIFEDIPINE FORMULATIONS AND USES THEREOF

CROSS-REFERENCE TO RELATED APPLICATIONS

The present application claims the benefit of priority from co-pending U.S. Provisional Patent Application No. 62/512,431 filed on May 30, 2017, and Canadian Patent Application No. 2,968,861 filed May 30, 2017, the contents of both of which are incorporated herein by reference in their entirety.

FIELD

The present application relates to topical nifedipine formulations comprising a photostabilizing effective amount of quercetin or a photostabilizing effective amount of a combination of quercetin and butyl methoxydibenzoylmethane (BMDBM) and to uses of such topical formulations, for example, to treat diseases, disorders or conditions that benefit from topical administration of nifedipine such as Raynaud phenomenon.

BACKGROUND

Raynaud Phenomenon (RP) causes vasospasm of the thermoregulatory arterioles in cold-exposed hands and feet of affected persons, resulting in numb, ischemic digits and pain, adversely affecting quality of life[1] and there is currently no effective topical product available to patients for acute treatment or for prevention. A characteristic blanching with clear demarcation occurs, accompanied by numbness and discomfort occurring due to ischemia, followed by bluish discoloration then redness when blood flow returns (hyperemia). After a cold challenge, recovery of perfusion is slower in RP patients. The nipple of the breast may also be affected very painfully.

Causes of RP include autoimmune disorders such as but not limited to: scleroderma, systemic lupus erythematosus, mixed connective-tissue disease, dermatomyositis, polymyositis, rheumatoid arthritis and Sjögren syndrome.[2] According the Scleroderma Association of Saskatchewan, RP affects approximately 90% of people with scleroderma.[3] Lupus erythematosus, affecting about 1 in 1000 Canadians, can also present with symptoms of Raynaud phenomenon.[4] An association with some medications, diabetes and occupational vibration exposure has also been noted. Primary RP (not related to connective tissue disease) also affects at least 3-7% of the population worldwide. For example, some drugs, including beta blockers (which may be used to treat high blood pressure), migraine medications that contain ergotamine or sumatriptan, attention-deficit/hyperactivity disorder medications, certain chemotherapy agents, and drugs that cause blood vessels to narrow (such as some over-the-counter cold medications) have been linked to Raynaud's phenomenon.

There may be familial tendency in some cases and it is more common in adult females.[1,5] While not wishing to be limited by theory, the pathogenesis of primary RP involves peripheral alpha-2 adrenoreceptors[5(b)] and disorders of the vascular system's thermoregulatory mechanisms.[6] Family history, migraines and smoking are also related to the incidence of primary RP.[1]

RP is always not a benign condition: in severe cases associated with certain connective tissue or autoimmune diseases, diabetes and/or drug exposures, tissue damage with ulceration and even necrosis may occur due to repeated and prolonged ischemia. For example, most patients with scleroderma suffer severe RP requiring medical treatment.[7] A survey of 443 subjects with self-reported RP from 15 countries found that 64 percent of subjects reported a poor or very poor current ability to prevent or control RP attacks.[8] Cold avoidance may not even be possible, for example, in patients with certain occupations.

When pharmacological treatment is initiated due, for example, to severe disease impact on quality of life, when preventative measures are insufficient and/or when tissue damage such as ulceration is occurring, an object of therapy is to reduce the severity and/or frequency of attacks.[9] For example, patients with secondary RP (disease-related, e.g. 90% of patients with scleroderma) are more likely to have severe attacks and require pharmacologic treatment[10], including oral vasodilators, calcium channel blockers[11], oral or topical nitrates, fluoxetine, phosphodiesterase-5 inhibitors[12], beta-blockers and local injections of botulinum A toxin.[13] Surgical sympathectomy of the hands may be used in resistant cases.[14] Oral calcium channel blockers are often front-line therapy for RP[15], and evidence-based reviews of the effectiveness of calcium channel blockers indicate that nifedipine appears to be superior to nicardipine in that drug class in reducing the frequency and severity of attacks in primary RP[16], whereas reviews of oral vasodilators show very limited effectiveness.[17] However, oral nifedipine has several constraints. To be effective, it must be taken on a daily basis but there is a risk of systemic adverse effects, such as flushing or dizziness, and the drug may not be as effective at a more tolerable dose. During an attack, oral dosing may not result in rapid relief due to the lag time for absorption.

A topical formulation for immediate as-needed use in patients with RP may avoid daily oral dosing, or could be used, for example as an adjunct therapy in more severe cases. An advantage of topical application of nifedipine would be that an immediate effect may, for example, be achieved on the local tissue and systemic exposure would be limited. However, for treatment of RP with topical agents, there is little available. Chung et al. performed a double-blind placebo controlled trial of a topical nitroglycerin product in patients with RP. While they found a significant difference between treatment and placebo in the clinical scoring of RP overall, there was no statistical difference in the duration, severity or subjective assessment of the RP attacks.[18] This is consistent with the lack of superiority of oral nitrates in the treatment of RP.[19] Nitrates, both topical and oral, are associated with headaches and flushing.[20] Furthermore, the well-known issue of pharmacological tolerance to nitrates with chronic dosing[21] has not been addressed in this clinical context. Nifedipine, however, does have good evidence of efficacy and its mechanism in RP is well understood.[22]

Local pharmacy-prepared topical nifedipine has sometimes been requested by physicians for use by patients but it was not stable due to the UV-light sensitivity of the drug, leading to inconsistent efficacy.[23] Furthermore, nifedipine is not water soluble, which may, for example, present certain limitations to the pharmacist such as having to use hydrophobic cream bases or having to perform relatively complex compounding procedures.

In general, a topical formulation is used either to treat the skin itself or as an alternative to other dosing routes for local tissues. The outermost layer of skin, the stratum corneum, is a barrier to absorption. Drugs can penetrate the skin through hair follicles or, for very lipophilic and small molecules, pass directly through the epithelium, but this is very limited.

Penetration enhancers are compounds which facilitate transdermal drug absorption such as by affecting epithelial tight junctions,[24] and thus are commonly employed in topical formulations which are intended to facilitate drug passage into the dermal layer or beyond. For example, the penetration enhancer diethylene glycol monoethyl ether (Transcutol HP®) has an established safety record[25], regulatory approval for human use and ease of incorporation into emulsions.

An emulsion may, for example, allow certain actives to be readily incorporated into the internal oil phase, while a non-greasy feel is still achieved. For patient acceptability, an oily topical preparation is generally not desirable for use on the hands and feet. However, a potential concern with emulsions in general is the tendency for coalescence of the oil droplets of the internal phase. If this occurs, long-term stability is reduced. The composition and viscosity are features which may be used to minimize the potential for phase separation.

Topical medications are applied to external body surfaces and therefore have the potential for significant light exposure. Typically, these preparations are applied as a thin film, maximizing the surface area of the formulation to light and therefore the potential to interact with UV light. A recent analysis of topical products in the United States Pharmacopoeia and the European medicines databases indicated that up to 28% of approved drugs have the recommendation to protect the product from light[26] and the list of new drugs with this recommendation continues to grow.[27] While some drug products are simply inactivated by light exposure, resulting in subpotency, others may form photodegradation products with toxicities or unknown effects.[28] Exposure of nifedipine to UVA light results in the formation of dehydronifedipine followed by dehydronitrosonifedipine[29], compounds which are inactive as vasodilators. Variable amounts of UV-induced degradation of nifedipine occur during preparation and storage. Light exposure may also influence the physical and/or technical performance of a topical formulation, such as but not limited to changes in viscosity, precipitation of components, changes in emulsion droplet size affecting stability and/or changes in chemical degradation of materials.[26]

Photostabilizers are chemicals that filter UV energy by absorbing a certain range of high energy UV wavelengths and releasing the energy at a lower range. In doing so, however, the photostabilizers degrade unless used in combination. UV blockers include rutin and quercetin (antioxidant compounds found in fruits and vegetables)[30] and butyl methoxydibenzoylmethane (BMDBM; an approved sunscreen agent also known as avobenzone).[31] These compounds dissolve into the oil phase of an oil-in-water (o/w) emulsion. In addition to its use as a photostabilizer, quercetin has also been used for wound healing[32].

Nifedipine may also be useful to treat conditions related to peripheral vascular insufficiency. Such conditions include venous leg ulceration due to sustained venous hypertension, which results from chronic venous insufficiency[33], intermittent claudication and peripheral arterial occlusive disease. The great majority of vascular ulcers are chronic or recurrent. They cause a considerable amount of morbidity among patients with peripheral vascular disease, including work incapacity. Additionally, these non-healing ulcers may place the patient at much higher risk for lower extremity amputation.

SUMMARY

A topical formulation of nifedipine has been prepared that was observed to be substantially stable to UVA light over the typical time period in which the nifedipine may be exposed to such light during use. This was accomplished by means of an oil-in-water emulsion containing ultraviolet (UV) light blockers (photostabilizers) such as quercetin and BMDBM. The topical nifedipine emulsion described herein had sufficient viscosity and an appropriate composition such that phase separation was not observed during the studies. The photostabilizer compounds dissolved into the oil phase of the oil-in-water (o/w) emulsion, where nifedipine was also solubilized.

Accordingly, the present application includes a topical formulation in the form of an oil-in-water emulsion comprising nifedipine and a photostabilizing effective amount of quercetin or a photostabilizing effective amount of a combination of quercetin and butyl methoxydibenzoylmethane (BMDBM).

In an embodiment, the oil phase further comprises glyceryl monostearate, stearic acid, liquid paraffin, petrolatum and diethylene glycol monoethyl ether. In another embodiment, in addition to water, the aqueous phase further comprises glycerin and sodium laurel sulfate.

The present application also includes a method for treating a disease, disorder or condition that benefits from topical administration of nifedipine, the method comprising topically administering an effective amount of a topical formulation of the present application to a subject in need thereof. The present application further includes a topical use of a topical formulation of the present application for treating a disease, disorder or condition that benefits from topical administration of nifedipine in a subject in need thereof, a use of a topical formulation of the present application for preparation of a topical medicament for treating a disease, disorder or condition that benefits from topical administration of nifedipine in a subject in need thereof as well as a topical formulation of the present application for topical use to treat a disease, disorder or condition that benefits from topical administration of nifedipine in a subject in need thereof.

In an embodiment, the disease, disorder or condition that benefits from topical administration of nifedipine is Raynaud's phenomenon.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

DRAWINGS

The embodiments of the application will now be described in greater detail with reference to the attached drawings in which:

FIG. 1 shows the ultraviolet (UV) absorption spectra of nifedipine in absorbance units as a function of wavelength (nm) for the following samples: nifedipine solution 40 µg/mL in methanol with peak absorbance at 348 nm (dotted line); methanol extract of nifedipine cream [2% (w/w) as oil-in-water (O/W) emulsion](dashed line); nifedipine solution after 2 h exposure to UVA light at a flux of 750 µW/cm$^2$ (alternating dotted and dashed line); and methanol extract of nifedipine cream [2% (w/w) as O/W emulsion] exposed for 2 h to UVA light at a flux of 750 µW/cm$^2$ (solid line) according to comparative examples of the present application.

FIG. 2 is a plot showing percent of original concentration of nifedipine as a function of time (14, 21, and 28 days) for nifedipine (N) 2% (w/w) cream prepared with or without Transcutol HP (T) [1% or 2% (w/w)] according to comparative examples of the present application which were stored protected from light at ambient temperature (23° C.) and concentration was measured by UV spectrophotometry. Data represent mean±SD (n=3).

Figure 8:
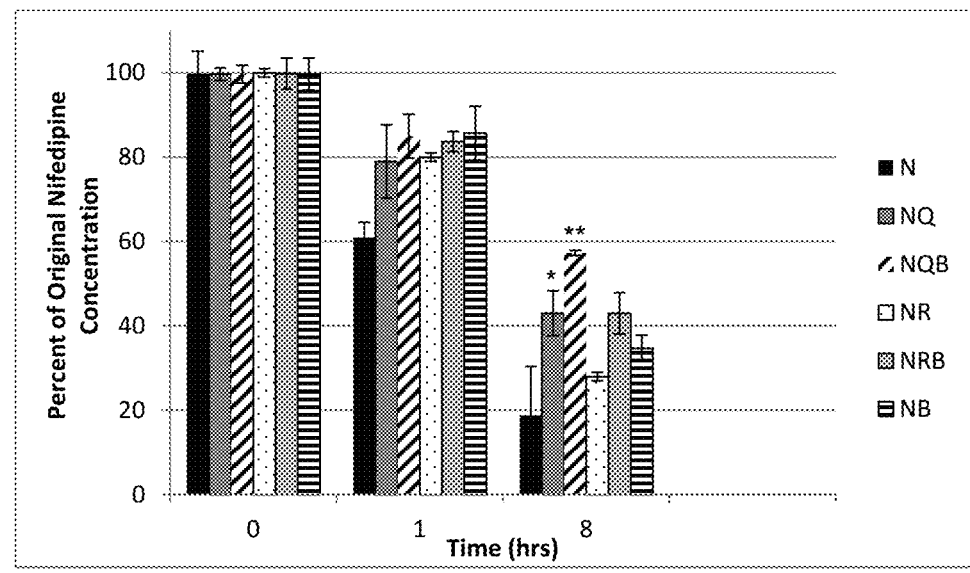

FIG. 8 is a plot showing the percent original nifedipine concentration as a function of time (hours) for creams with no added photoprotectant (N), with quercetin [0.5% (w/w)] (NQ), with quercetin [0.5% (w/w)] and BMDBM [3% (w/w)] (NQB), with rutin [3% (w/w)] (NR), with rutin [3% (w/w)] and BMDBM [3% (w/w)] (NRB) and with BMDBM [3% (w/w)] (NB) incorporated into a nifedipine 2% (w/w) cream as a photostabilizer according to examples of the topical formulations of the present application. The cream was exposed as a thin film to UVA light Flux=750 μW/cm.$^2$ Data represent mean±SD (n=3). *indicates statistically significant difference (p<0.05) from nifedipine cream with no photostabilizers. ** indicates statistically significant difference from nifedipine cream with quercetin only or rutin only or BMDBM only (p<0.05).

Figure 9:
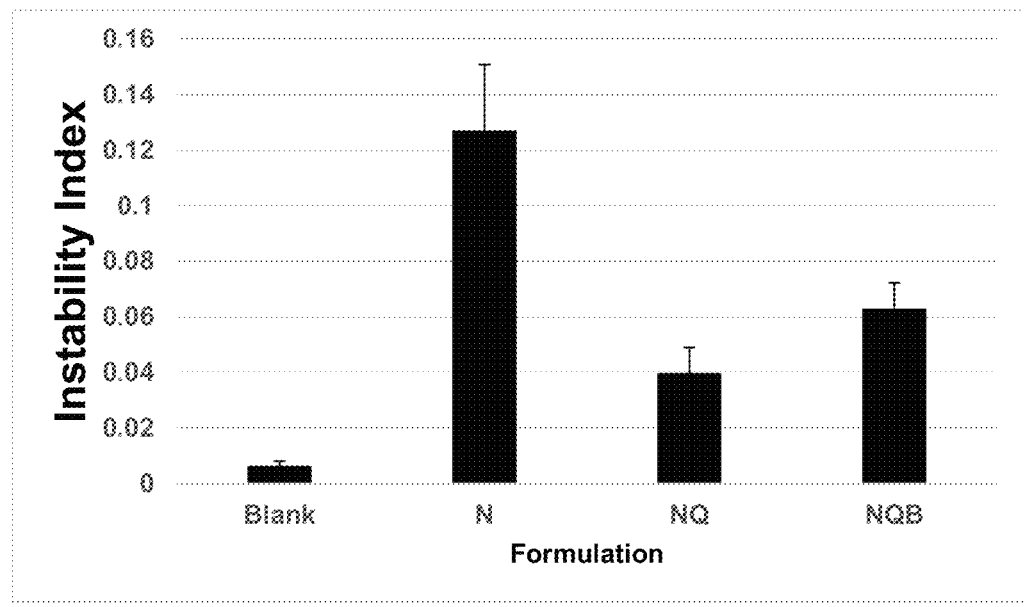

FIG. 9 contains results of sedimentation analysis of a nifedipine emulsion (N) according to a comparative example of the present application as well as nifedipine emulsions containing quercetin (NQ) or quercetin plus BMDBM (NQB) according to examples of the topical formulations of the present application showing differences in their tendency to exhibit phase separation (42° C. over 12 hrs), as shown by an increase in light transmission at the top of the sample as the oil phase separates to the top. This rate of change in light transmission of the sample vs time was translated into an "instability index", where a greater rate of phase separation is considered greater instability.

Figure 10:
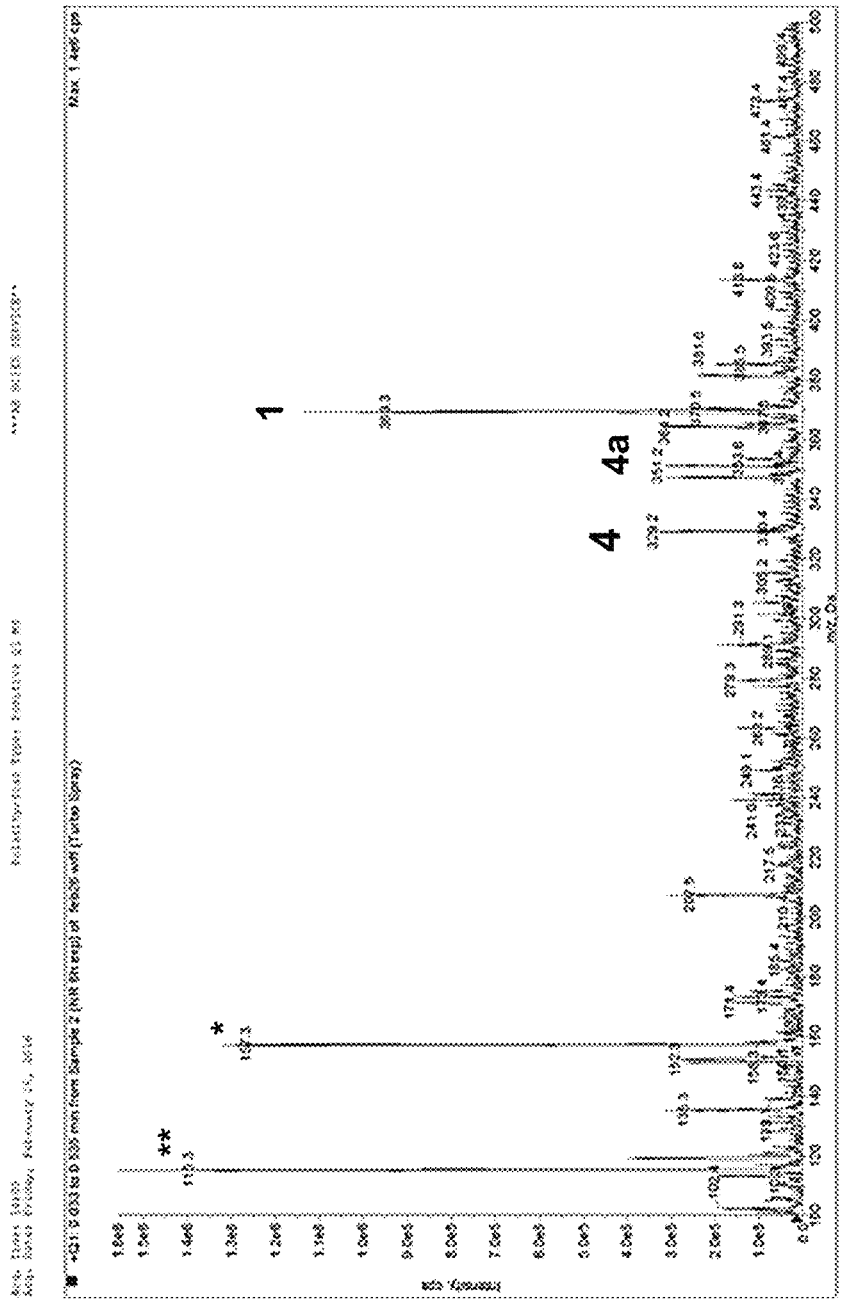

FIG. 10 is a Q1 scan of nifedipine extracted from nifedipine 2% w/w cream containing rutin [2% w/w)] with UVA exposure for 6 hrs as thin film at 492 μW/cm$^2$ according to a comparative example of the present application indicating that dehydronifedipine and dehydronitrosonifedipine are the main photodegradants of nifedipine in the emulsion formulation, based on appearance of m/z consistent with their expected profiles upon UV exposure of the emulsion.

Figure 11:
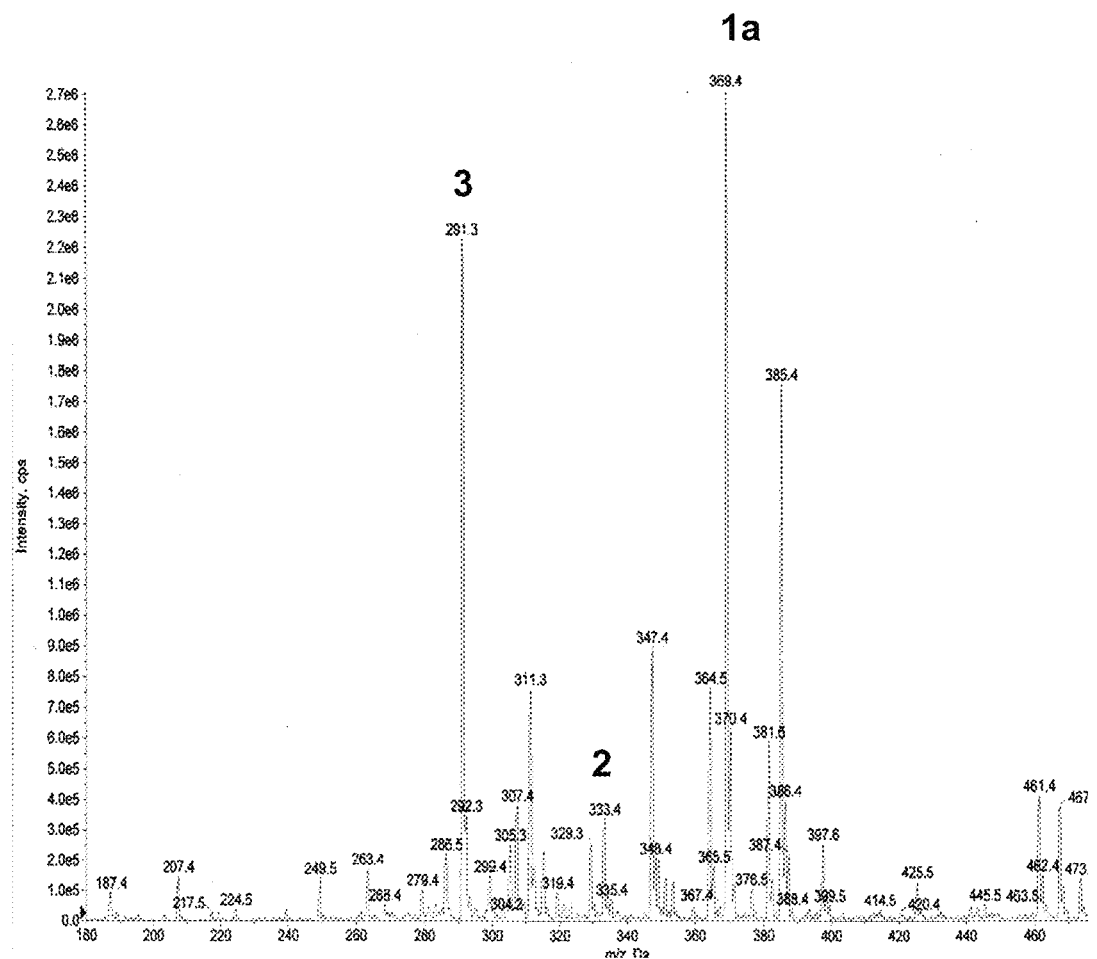

FIG. 11 is a mass spectrum showing the appearance of nifedipine 2% w/w cream containing 0.5% w/w quercetin and BMDBM [3% (w/w)] according to an example of the topical formulations of the present application subsequent to exposing a thin film of the cream to UVA ($_{492}$ μW/cm$^2$) for 6 hrs.

Figure 12:
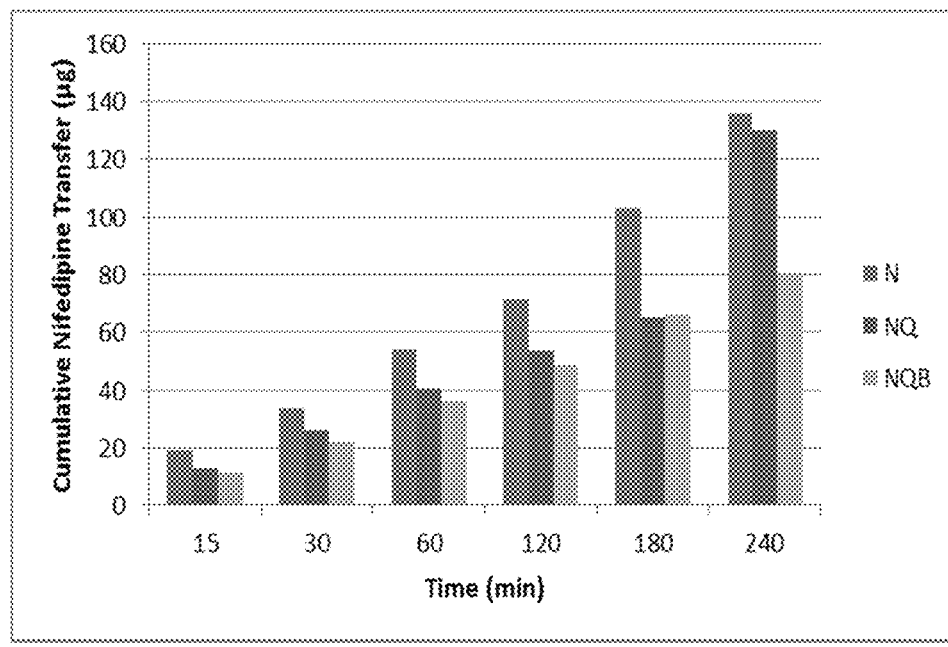

FIG. 12 is a plot comparing the absorption of nifedipine across a model skin membrane in a vertical diffusion apparatus showing a linear trend of accumulation over time (minutes) at a temperature of 32° C. for nifedipine emulsions with quercetin (NQ) or with BMDBM (NB) according to examples of the topical formulations of the present application; or without these photostabilizers (N) according to a comparative example of the present application.

DETAILED DESCRIPTION

I. Definitions

Unless otherwise indicated, the definitions and embodiments described in this and other sections are intended to be applicable to all embodiments and aspects of the present application herein described for which they are suitable as would be understood by a person skilled in the art.

The present application refers to a number of chemical terms and abbreviations used by those skilled in the art. Nevertheless, definitions of selected terms are provided for clarity and consistency.

As used herein, the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process/method steps. As used herein, the word "consisting" and its derivatives, are intended to be close ended terms that specify the presence of stated features, elements, components, groups, integers, and/or steps, and also exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of these features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

As used in this application, the singular forms "a", "an" and "the" include plural references unless the content clearly dictates otherwise. For example, an embodiment including "a penetration enhancer" should be understood to present certain aspects with one penetration enhancer or two or more additional penetration enhancers. In embodiments comprising an "additional" or "second" component, such as an additional or second penetration enhancer, the second component as used herein is chemically different from the other components or first component. A "third" component is different from the other, first, and second components, and further enumerated or "additional" components are similarly different.

The term "and/or" as used herein means that the listed items are present, or used, individually or in combination. In effect, this term means that "at least one of" or "one or more" of the listed items is used or present.

The terms "butyl methoxydibenzoylmethane", "BMDBM" and "avobenzone" as used herein refer to the compound having the IUPAC name 1-(4-methoxyphenyl)-3-[4-(2-methyl-2-propanyl)phenyl]-1,3-propanedione and the following structure:

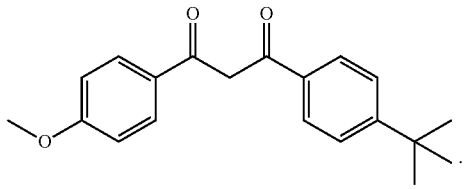 [SMILES: COc1ccc(C(=O)CC(=O)c2ccc(C(C)(C)C)cc2)cc1]

The term "quercetin" as used herein refers to the compound having the IUPAC name 2-(3,4-dihydroxyphenyl)-3,5,7-trihydroxy-4H-chromen-4-one and the following structure:

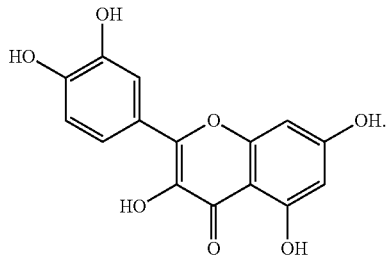 [SMILES: O=c1c(O)c(-c2ccc(O)c(O)c2)oc2cc(O)cc(O)c12]

The term "rutin" as used herein refers to the compound having the IUPAC name 2-(3,4-dihydroxyphenyl)-5,7-dihydroxy-4-oxo-4H-chromen-3-yl 6-O-(6-deoxy-α-L-mannopyranosyl)-β-D-glucopyranoside and the following structure:

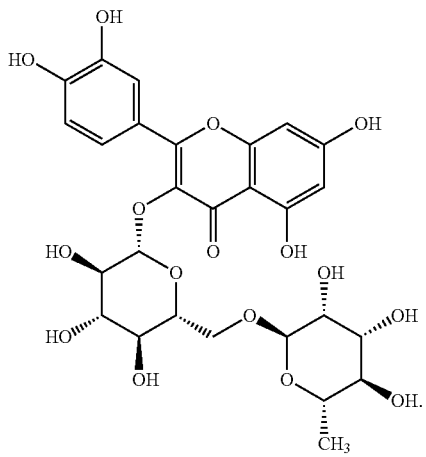 [SMILES: C[C@@H]1O[C@@H](OC[C@H]2O[C@@H](Oc3c(-c4ccc(O)c(O)c4)oc4cc(O)cc(O)c4c3=O)[C@H](O)[C@@H](O)[C@@H]2O)[C@H](O)[C@H](O)[C@H]1O]

The term "subject" as used herein includes all members of the animal kingdom including mammals, and suitably refers to livestock (such as but not limited to bovines) and humans. In an embodiment, the subject is a mammal. In another embodiment, the subject is human. In a further embodiment, the subject is livestock. It is an embodiment that the livestock is a bovine.

The terms "oil-in-water emulsion" and "O/W emulsion" and the like as used herein refer to a mixture of two liquid phases, an oil phase and an aqueous phase wherein the oil phase is dispersed in the aqueous phase; i.e. the oil phase is the "dispersed phase" and the aqueous phase is the "continuous phase".

The terms "formulation" and "pharmaceutical formulation" as used herein are equivalent terms referring to a formulation for pharmaceutical use.

The term "for pharmaceutical use" means compatible with the treatment of subjects, for example mammals such as livestock and humans.

The terms "treating" or "treatment" and the like as used herein and as is well understood in the art, means an approach for obtaining beneficial or desired results, including clinical results. Beneficial or desired clinical results include, but are not limited to alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable. "Treating", "treatment" and the like as used herein also include prophylactic treatment. Treatment methods and uses comprise topically administering to a subject or topical use of, respectively, an effective amount of nifedipine and optionally consist of a single administration or use, or alternatively comprise a series of administrations or uses. For example, the nifedipine is topically administered or used at least once a week. However, in another embodiment, the nifedipine is topically administered to the subject or used from about one time per two weeks, three weeks or one month. In another embodiment, the nifedipine is topically administered or used about one time per week to about once daily. In another embodiment, the nifedipine is topically administered or used 2, 3, 4, 5 or 6 times daily. The length of the treatment period depends on a variety of factors, such as the type and/or severity of the disease, disorder or condition, the age of the subject, the concentration of the nifedipine in the topical formulation, and/or a combination thereof. It will also be appreciated that the effective dosage of the nifedipine used for the treatment may increase or decrease over the course of a particular treatment regime. Changes in dosage may result and become apparent by standard diagnostic assays known in the art. In some instances, chronic administration or use is required. For example, the nifedipine is topically administered to the subject or used in an amount and for duration sufficient to treat the subject. In an embodiment, the nifedipine is for immediate as-needed topical administration or use.

"Palliating" a disease, disorder or condition means that the extent and/or undesirable clinical manifestations of the disease, disorder or condition are lessened and/or time course of the progression is slowed or lengthened, as compared to not treating the disease, disorder or condition.

The term "prevention" or "prophylaxis", or synonym thereto, as used herein refers to a reduction in the risk or probability of a subject becoming afflicted with a disease, disorder or condition or manifesting a symptom associated with a disease, disorder or condition.

As used herein, the terms "effective amount" or "therapeutically effective amount" mean an amount of nifedipine that is effective, at dosages and for periods of time necessary to achieve the desired result. For example in the context of treating Reynaud's phenomenon, an effective amount is an amount that, for example, decreases vasospasm of the thermoregulatory arterioles in cold-exposed extremities in the presence of treatment in comparison to the vasospasm of the thermoregulatory arterioles in cold-exposed extremities in the absence of treatment. In an embodiment, effective amounts vary according to factors such as the disease state, age, sex and/or weight of the subject. In a further embodiment, the amount of nifedipine that will correspond to an effective amount will vary depending upon factors, such as the type of condition, disease or disorder, the identity of the subject being treated, and the like, but can nevertheless be routinely determined by one skilled in the art.

The "disease, disorder or condition" as used herein refers to a disease, disorder or condition that benefits from topical administration of nifedipine.

The term "topical formulation" as used herein includes a composition that is suitable for topical application to the skin, nail, mucosa, wound bed or wound cavity. Topical formulations may be used, for example, for local, regional, or transdermal application of substances.

The terms "topical administration" or "topical use" as used herein include the delivery of nifedipine to the skin or a localized region of the body as well as transdermal delivery of nifedipine through the skin.

The term "penetration enhancer" as used herein refers to a compound or mixture of compounds that improves the rate of percutaneous transport of nifedipine across the skin for use and delivery of nifedipine to subjects such as mammals, for example, humans.

The term "emulsifier" as used herein refers to a compound or mixture of compounds which promotes or facilitates the dispersion of one substance in another to form an emulsion.

The term "emulsion stabilizer" as used herein refers to a compound or mixture of compounds that helps to maintain the oil-in-water emulsion.

The term "moisturizer" as used herein refers to a compound or mixture of compounds that makes the external layers of the skin (epidermis) softer, more pliable and/or increases its hydration by reducing evaporation.

The term "solvent" as used herein refers to a liquid or mixture of liquids which aids in dissolving and/or diluting any other component or mixture of components in the topical formulation.

The term "emollient" as used herein refers to a compound or mixture of compounds that adds or replaces natural oils in the skin, for example by maintaining the integrity of the hydrolipids of the skin.

The term "thickener" as used herein refers to a compound or mixture of compounds that adjusts the thickness of the topical formulation.

The term "humectant" as used herein refers to a compound or mixture of compounds to increase the water content of the top layers of skin.

The term "surfactant" as used herein refers to an amphiphilic compound or mixture of amphiphilic compounds that lowers the surface tension (or interfacial tension) between two liquids or between a liquid and a solid.

The term "anionic surfactant" as used herein refers to a surfactant that contains an anionic functional group at its head such as but not limited to sulfate, sulfonate, phosphate and carboxylate.

The term "water" as used herein as an ingredient in the topical formulations of the application refers to pharmaceutically acceptable water.

The term "% w/w" means a percentage expressed in terms of weight of a component over the total weight of a formulation multiplied by 100.

The term "photostabilizing effective amount of quercetin" as used herein refers to an amount of quercetin that, when added to a topical formulation of the present application, will substantially inhibit photodegradation of nifedipine over the time period the topical formulation is exposed to light during topical administration or use for treatment of a disease, disorder or condition that benefits from topical administration of nifedipine.

The term "photostabilizing effective amount of a combination of quercetin and butyl methoxydibenzoylmethane (BMDBM)" as used herein refers to an amount of quercetin and BMDBM that, when added to a topical formulation of the present application, will substantially inhibit photodegradation of nifedipine over the average time period the topical formulation is exposed to light during topical administration or use for treatment of a disease, disorder or condition that benefits from topical administration of nifedipine.

II. Topical Formulations and Processes for their Preparation

Topical nifedipine oil-in-water emulsions have been prepared. In stability studies, nifedipine concentration was maintained at >95% of original concentration at 23° C. or 4° C. for at least 12 months protected from light. However, upon exposure to indoor fluorescent room light appearance of the major degradation product, dehydronitrosonifedipine (DHN) appeared within 2 hours. Rutin, quercetin and a combination of BMDBM and quercetin were incorporated at varying concentrations in the emulsion. While rutin was not effective, quercetin and the combination of quercetin and BMDBM increased the stability of nifedipine to UVA light. For example, when quercetin (0.5% w/w) was incorporated into the nifedipine cream, photostability was improved after UVA exposure. In combination with BMDBM, a further improvement to at least 75% at 492 $\mu W/cm^2$ or at least 55% at 750 $\mu W/cm^2$ of the original concentration even after 8 h of UVA exposure was observed. Mass spectrometry was used to determine which nifedipine degradation products occurred following UV exposure when the photostabilizers (rutin, quercetin or a combination of quercetin and BMDBM) were present. Dehydronifedipine and dehydronitrosonifedipine were found in UVA-exposed creams, with no alternative degradation pathways identified in the presence of these photostabilizers. To study if these additional excipients might reduce the physical stability of the emulsion by affecting viscosity or emulsion droplet formation, the creaming rate and extent were assessed in a temperature-controlled photocentrifuge whereby an increased transmission to light indicates phase separation, which was then calculated as an instability index. The incorporation of quercetin or BMDBM increased the stability of the nifedipine emulsion in comparison to the emulsion without the presence of these photostabilizers. There was no visible phase separation even at 24 months at ambient temperature. To assess the permeability of nifedipine to model skin membranes (StratM membranes), a Franz-type static diffusion cell apparatus was used and diffusion of nifedipine at 32° C. from the emulsion to the receptor compartment (comprised of saline and 20% ethanol to permit drug solubility) was determined. The drug did diffuse for all samples including those with the photostabilizer quercetin or the combination of quercetin and BMDBM.

Accordingly, the present application includes a topical formulation in the form of an oil-in-water emulsion comprising nifedipine and a photostabilizing effective amount of quercetin or a photostabilizing effective amount of a combination of quercetin and butyl methoxydibenzoylmethane (BMDBM). In an embodiment, the topical formulation comprises a photostabilizing effective amount of quercetin. In another embodiment, the topical formulation comprises a photostabilizing effective amount of a combination of quercetin and butyl methoxydibenzoylmethane (BMDBM).

In an embodiment, the topical formulation further comprises one or more of: penetration enhancer, emulsifier, emulsion stabilizer, moisturizer, solvent, emollient, thickener, humectant and surfactant. The penetration enhancer, emulsifier, emulsion stabilizer, moisturizer, solvent, emollient, thickener, humectant and/or surfactant for use in the topical formulations of the present application can be any suitable penetration enhancer, emulsifier, emulsion stabilizer, moisturizer, solvent, emollient, thickener, humectant and/or surfactant, the selection of which can be made by a person skilled in the art.

The selection of a suitable surfactant is made, for example based on its hydrophilic-lipophilic balance (HLB), a measure of the degree to which the surfactant is hydrophilic or lipophilic and which can be used to predict the surfactant values of the surfactant. Ionic surfactants have been assigned relative HLB values, allowing the range of numbers to extend from 0-60. For example, sodium lauryl sulfate has an HLB value of 40. Surfactants having similar HLB values may be substituted for each other. HLB values are readily available and/or can be calculated by a person skilled in the art.

In an embodiment, the surfactant is an anionic surfactant. In another embodiment, the anionic surfactant is a sulfonate. In a further embodiment, the surfactant has an HLB value of from about 30 to about 50 or about 40.

In an embodiment of the present application, the formulation further comprises glyceryl monostearate, stearic acid, liquid paraffin, petrolatum and diethylene glycol monoethyl ether. In an embodiment these ingredients are added in the oil phase.

In another embodiment,
the glyceryl monostearate is present in the topical formulation in an amount of from about 5% w/w to about 10% w/w;
the stearic acid is present in the topical formulation in an amount of from about 5% w/w to about 15% w/w;
the liquid paraffin is present in the topical formulation in an amount of from about 5% w/w to about 15% w/w;
the petrolatum is present in the topical formulation in an amount of from about 5% w/w to about 15% w/w; and
the diethylene glycol monoethyl ether is present in the topical formulation in an amount of from about 0.1% w/w or about 0.5% w/w to about 3% w/w, all values for % w/w being based on the total weight of the topical formulation.

In an embodiment, in addition to water, the formulation further comprises glycerin and an anionic surfactant such as sodium laurel sulfate. In an embodiment the glycerin and anionic surfactant are added in the water or aqueous phase.

In another embodiment,
the water is present in the topical formulation in an amount of from about 45% w/w to about 60% w/w;

the glycerin is present in the topical formulation in an amount of from about 10% w/w to about 20% w/w; and
the anionic surfactant, for example sodium laurel sulfate is present in the topical formulation in an amount of from about 0.1% w/w to about 2% w/w, all values for % w/w being based on the total weight of the topical formulation.

In an embodiment, the nifedipine is present in the topical formulation in an amount of from about 0.1% w/w to about 5% w/w, from about 0.5% w/w to about 3% w/w or from about 1.0% w/w to about 2.0% w/w based on the total weight of the topical formulation. In another embodiment, the nifedipine is present in the topical formulation in an amount of from about 0.5% w/w to about 1.5% w/w or from about 1.5% w/w to about 2.5% w/w based on the total weight of the topical formulation. In a further embodiment, the nifedipine is present in an amount of about 2% w/w, based on the total weight of the topical formulation.

In an embodiment, the quercetin is present in the topical formulation in an amount of from about 0.1% w/w to about 3% w/w, from about 0.2% w/w to about 2% w/w or from about 0.25% w/w to about 0.75% w/w based on the total weight of the topical formulation. In another embodiment, the quercetin is present in an amount of about 0.5% w/w, based on the total weight of the topical formulation.

In an embodiment, the BMDBM is present in the topical formulation in an amount of from about 0.1% w/w to about 4% w/w, from about 1.0% w/w to about 3.5% w/w or about 2.0% w/w to about 3.0% w/w based on the total weight of the topical formulation. In another embodiment, the BMDBM is present in an amount of about 3% w/w, based on the total weight of the topical formulation In an embodiment, greater than about 60% w/w, greater than about 70% w/w or greater than about 75% w/w of the nifedipine in the topical formulation is present after exposing a thin film of the topical formulation to ultraviolet A (UVA) radiation at a flux of about 492 $\mu W/cm^2$ for about 8 hours. In another embodiment, about 80% w/w of the nifedipine in the topical formulation is present after exposing a thin film of the topical formulation to ultraviolet A (UVA) radiation at a flux of about 492 $\mu W/cm^2$ for about 8 hours. In an embodiment, at least 55% w/w of the nifedipine in the topical formulation is present after exposing a thin film of the topical formulation to ultraviolet A (UVA) radiation at a flux of about 750 $\mu W/cm^2$ for about 8 hours. The term "thin film" as used herein in reference to these embodiments refers to the film created by applying a 20 mg sample of the topical formulation to a surface of 15 mm×15 mm.

In an embodiment, the topical formulation is in the form of a cream.

In an embodiment, the topical formulation is formulated for transdermal delivery of the nifedipine to the subject.

The topical formulations of the present application are prepared by conventional methods for preparing an oil-in-water emulsion for pharmaceutical use. In an embodiment, the topical formulation is prepared by a method comprising:

(a) mixing the desired amounts of all components of the oil phase other than the nifedipine, the quercetin and the BMDBM, if present (e.g. mixing glyceryl monostearate, stearic acid, liquid paraffin, petrolatum and diethylene glycol monoethyl ether) together for a time and at a temperature (e.g. about 75° C. to about 90° C. or about 85° C.) to obtain a homogeneous mixture, then mixing the desired amounts of the nifedipine, the quercetin and the BMDBM, if present into the oil phase until a homogeneous oil phase is obtained;

(b) mixing the desired amounts of all components of the aqueous phase (e.g. mixing water, glycerin and sodium laurel sulfate) for a time and at a temperature (e.g. about 75° C. to about 95° C. or about 85° C.) to obtain a homogeneous water phase;

(c) adding the homogeneous water phase to the homogeneous oil phase, and mixing for a time and at a temperature (e.g. about 75° C. to about 90° C. or about 85° C.) to obtain an emulsion then reducing the temperature to about 30° C. to about 50° C. or about 40° C., while stirring, followed by homogenizing for a time of about 1 minute to about 10 minutes or about 5 minutes; and (d) cooling to ambient temperature (e.g. about 18° C. to about 23° C.).

The topical formulations of the present application are preferably stored before use protected from light and moisture loss (e.g. in an opaque plastic container).

III. Methods and Uses

The topical administration of nifedipine may, for example, be useful for the treatment of various diseases, disorders or conditions including Raynaud's phenomenon, chilblains and wounds.

Accordingly, the present application also includes a method for treating a disease, disorder or condition that benefits from topical administration of nifedipine, the method comprising topically administering an effective amount of a topical formulation of the present application to a subject in need thereof. The present application further includes a topical use of a topical formulation of the present application for treating a disease, disorder or condition that benefits from topical administration of nifedipine in a subject in need thereof, a use of a topical formulation of the present application for preparation of a topical medicament for treating a disease, disorder or condition that benefits from topical administration of nifedipine in a subject in need thereof as well as a topical formulation of the present application for topical use to treat a disease, disorder or condition that benefits from topical administration of nifedipine in a subject in need thereof.

In an embodiment, the disease, disorder or condition that benefits from topical administration of nifedipine is Raynaud's phenomenon.

Accordingly, the present application also includes a method for treating Raynaud's phenomenon, the method comprising topically administering an effective amount of a topical formulation of the present application to a subject in need thereof. The present application further includes a topical use of a topical formulation of the present application for treating Raynaud's phenomenon in a subject in need thereof, a use of a topical formulation of the present application for preparation of a topical medicament for treating Raynaud's phenomenon in a subject in need thereof as well as a topical formulation of the present application for topical use to treat Raynaud's phenomenon in a subject in need thereof.

In an embodiment, the Raynaud's phenomenon is primary Raynaud's phenomenon. In another embodiment, the Raynaud's phenomenon is caused by an autoimmune disorder. In an embodiment, the autoimmune disorder is selected from scleroderma, systemic lupus erythematosus, mixed connective-tissue disease, dermatomyositis, polymyositis, rheumatoid arthritis and Sjögren syndrome. In a further embodiment, the Raynaud's phenomenon is associated with administration of a medication, diabetes or occupational vibration exposure.

In another embodiment, the disease, disorder or condition that benefits from topical administration of nifedipine is chilblains.

Accordingly, the present application also includes a method for treating chilblains, the method comprising topically administering an effective amount of a topical formulation of the present application to a subject in need thereof. The present application further includes a topical use of a topical formulation of the present application for treating chilblains in a subject in need thereof, a use of a topical formulation of the present application for preparation of a topical medicament for treating chilblains in a subject in need thereof as well as a topical formulation of the present application for topical use to treat chilblains in a subject in need thereof.

In a further embodiment, the disease, disorder or condition that benefits from topical administration of nifedipine is a wound.

Accordingly, the present application also includes a method for treating a wound, the method comprising topically administering an effective amount of a topical formulation of the present application to the wound of a subject in need thereof. The present application further includes a topical use of a topical formulation of the present application for treating a wound in a subject in need thereof, a use of a topical formulation of the present application for preparation of a topical medicament for treating a wound in a subject in need thereof as well as a topical formulation of the present application for topical use to treat a wound in a subject in need thereof.

In some embodiments, the topical administration or use (as the case may be) of the topical formulation reduces scarring in an incisional wound.

In some embodiments, the wound is a diabetic ulcer, a scleroderma-associated ulcer, a pressure sore or an anal fissure.

In yet a further embodiment, the disease, disorder or condition that benefits from topical administration of nifedipine is a condition related to peripheral vascular insufficiency.

Accordingly, the present application also includes a method for treating a condition related to peripheral vascular insufficiency, the method comprising topically administering an effective amount of a topical formulation of the present application to a subject in need thereof. The present application further includes a topical use of a topical formulation of the present application for treating a condition related to peripheral vascular insufficiency in a subject in need thereof, a use of a topical formulation of the present application for preparation of a topical medicament for treating a condition related to peripheral vascular insufficiency in a subject in need thereof as well as a topical formulation of the present application for topical use to treat a condition related to peripheral vascular insufficiency in a subject in need thereof.

In an embodiment of the present application, the condition related to peripheral vascular insufficiency is venous leg ulceration, intermittent claudication and peripheral arterial occlusive disease.

In an embodiment, the disease, disorder or condition that benefits from topical administration of nifedipine is bovine hock lesions.

Accordingly, the present application also includes a method for treating bovine hock lesions, the method comprising topically administering an effective amount of a topical formulation of the present application to a subject in need thereof. The present application further includes a topical use of a topical formulation of the present application for treating bovine hock lesions in a subject in need thereof, a use of a topical formulation of the present application for preparation of a topical medicament for treating bovine hock lesions in a subject in need thereof as well as a topical formulation of the present application for topical use to treat bovine hock lesions in a subject in need thereof.

The following non-limiting examples are illustrative of the present application:

EXAMPLES

Example 1: UV-Stabilized Topical Formulation of Nifedipine

I Materials and Methods

Chemicals: Glyceryl monostearate (GL149) was purchased from Spectrum. Stearic acid (Kolliwax™ S) and glycerin (Kollisolv™ G99) were from BASF. Liquid paraffin, rutin (>94%), quercetin (>95%) and white petrolatum (Vaseline™) were from Sigma-Aldrich Canada, and mixed tocopherols from Lotioncrafters. Sodium lauryl sulphate was from BioRad. Nifedipine (>98%) was from Alpha Aesar. Butyl methoxydibenzoylmethane (BMDBM) was purchased from Tokyo Chemical Industries. Transcutol™ P (diethylene glycol monoethyl ether) was from Gattefosse Canada. Water was purified by reverse osmosis (MilliQ system). Analytical reference standards of nifedipine and dehydronitrosonifedipine were from Sigma-Aldrich (99% purity).

Preparation of Topical Nifedipine: Topical nifedipine was prepared as an oil-in-water emulsion using the beaker method, where nifedipine was incorporated into the internal oil phase. Nifedipine is light-sensitive therefore work was conducted under yellow light, which does not cause photodegradation.

For the oil phase, glyceryl monostearate (6.7% w/w), stearic acid (9.5% w/w), liquid paraffin (9.5% w/w), petrolatum (9.5% w/w) and Transcutol P (2% w/w) were weighed into a 250 mL beaker and warmed in a water bath on a hotplate to 85° C. with stirring until homogeneous, followed by addition of the nifedipine (2% w/w). Where indicated, the following additives were included in the oil phase: quercetin (0.5-3% w/w), rutin (0.5-3% w/w) and/or BMDBM (0.5-3% w/w).

For the water phase, Milli-Q purified water (46% w/w), glycerin (13.4% w/w), and sodium lauryl sulfate (0.95% w/w) were warmed in a second beaker to 85° C. in a water bath with stirring.

The water phase was added to the warmed oil phase slowly with continuous stirring, and within a few minutes, emulsion formation was noted by a visual change to opacity as well as a sudden increase in viscosity. The emulsion in the water bath was removed from heat and stirring continued while cooling slowly in the water bath until reaching 40° C., followed by homogenization for 5 min, then allowed to cool completely at ambient temperature (18-21° C.). Prepared creams were protected from light and stored at 4° C.

Values provided for % w/w for all components other than quercetin, rutin and BMDBM are based on a 2% w/w concentration of nifedipine and no photoprotectant in the formulation. Accordingly, these values will vary based on the amount of quercetin, rutin and BMDBM added. Values provided for quercetin, rutin and BMDBM are based on the total weight of the preparation.

Light Exposure: A UVA lamp was mounted 8.5 inches above a lab bench surface and the flux set to 740-750 $\mu W/cm^2$. This level of flux is roughly equivalent to a bright sunny day in mid-summer. Alternatively, where indicated, the flux was 492 $\mu W/cm^2$ which is more similar to UV exposure in Canada in summer. The lamp apparatus was placed inside an enclosure with an access door, to prevent ambient light entering and for worker safety. For samples exposed to "ambient light", these were placed on a laboratory bench where standard fluorescent lighting was used. Nifedipine 20 mg cream samples were spread evenly across the surface of a 15 mm×15 mm microscope coverslip to create a thin film. To prevent drying, the samples were covered with Saran Wrap®, a plastic film that was determined to be UVA-transparent. After the allotted exposure time the cream was scraped off the slide for extraction with methanol. Samples which were exposed while in solution and not incorporated in a cream were dissolved in methanol as a 20 mL solution in a 100 mL beaker.

Extraction of Nifedipine from the Cream: Solvent extractions were performed under yellow light. The sample was warmed in a water bath to 85° C. to melt lipids, followed by addition of 5 mL of methanol and vortex mixing. The samples were centrifuged at 14,000×g for 5 minutes and the supernatant retained for analysis. The extraction efficiency was 90%.

Spectrophotometric Assay: Nifedipine concentrations were measured in methanol on a UV spectrophotometer (Unico SQ-2800) at 348 nm. The linear range was 5-100 $\mu g/mL$ ($r^2>0.999$). Values reported represent mean±SD for triplicate measurements.

Stability Studies: Nifedipine cream was prepared in replicates of 50 g batches and stored at ambient (21° C.) or refrigerated (4° C.) temperatures, protected from light. At the indicated timepoints, triplicate samples of 1 g were removed and extracted as described above, followed by HPLC analysis.

High Performance Liquid Chromatography (HPLC) Assay: Nifedipine was quantified by reverse-phase HPLC at ambient temperature (23° C.)—by an isocratic method on a Waters 2690 instrument equipped with a photodiode array detector (Waters 996). The column was a C18 5 $\mu m$ 4.6×150 mm (Phenomenex) and the mobile phase was acetonitrile: sodium acetate (1 mM, pH 5.3) (70:30 v/v), generating a retention time of 2.9 min for nifedipine (linear range 10-100 $\mu g/mL$, $r^2>0.99$).

Drug Diffusion (Permeation Model): Vertical 9 mm Franz cells (PermeGear) with 5 mL glass receptor vials protected from light were mounted in a water-jacketed multi-cell magnetic stirring apparatus (Fisher Scientific) that permitted ease of sampling the receiver compartment and reloading it with media after each sampling. The Franz cells housed STRAT-M membranes (MilliPore), an established skin model.[34] Strat-M membranes are made up of polyethersulfone, polyolefin and skin lipids. A static rather than flow-through system was chosen to better model Raynaud's phenomenon. The donor media was nifedipine cream, 2 g. The receptor medium was a hydroalcoholic mixture to permit nifedipine solubility, composed of water, ethanol and buffering agent, pH 7.4. The receptor medium was maintained at 37° C. by means of a circulating water bath. For the static cells, 0.5 mL (representing 10% by volume) was removed for each sampling and immediately replaced by 0.5 mL of fresh receptor medium at 37° C. Samples were immediately analyzed by HPLC for nifedipine concentration. The apparent permeability coefficient of nifedipine in each cream formulation was calculated. The total amount of nifedipine transferred across the skin as well as the flux was calculated for samples with and without the penetration enhancer Transcutol HP.

Emulsion Phase Stability Analysis: A high-end Dispersion Analyser [LUMiSizer® (LUM GmbH)], which is a multi-sample, temperature-controlled analytical photocentrifuge with dedicated software, was used to predict long-term stability and optimization of nifedipine emulsions by means of creaming rate. This allows for an approximation of the relative stability to phase separation of emulsions that differ in the type or percentage of photoprotectant and for confirming batch-to-batch consistency in stability against phase separation.[35] For each sample type, triplicate samples of 2 mL were loaded into photocentrifuge acrylic cuvettes. The samples were centrifuged at 42° C.×12 hrs. Phase separation was detected as an increase in light transmission at the top of the sample, which is interpreted as an "instability index" reflecting the rate of change of light transmission.

Mass Spectrometry Analysis of Nifedipine and its Photdegradants: The high performance liquid chromatography (HPLC) MS/MS system was made up of an Agilent series 1200 quaternary pump with an online degasser, auto sampler set to 4 degrees C. and DAD detector scanning between 190 to 400 nm (Agilent Technologies) coupled to an AB Sciex API 4000 QTRAP mass spectrometer. Identification of the photodegradants of nifedipine following direct infusion of 2.5 ng was achieved through use of the transitions [M]1+ to [M-$C_{17}H_{16}N_2O_6$]+(m/z 345→344) for dehydronifedipine and [M]1+ to [M-$C_{17}H_{16}N_2O_5$]+(m/z 349→328) for dehydronitrosonifedipine; peak areas were integrated by Analyst Software v1.6 (SCIEX, Redwood City, Calif.).[36]

II. Results (a) Characterization of Topical Nifedipine Cream

Figure 1:
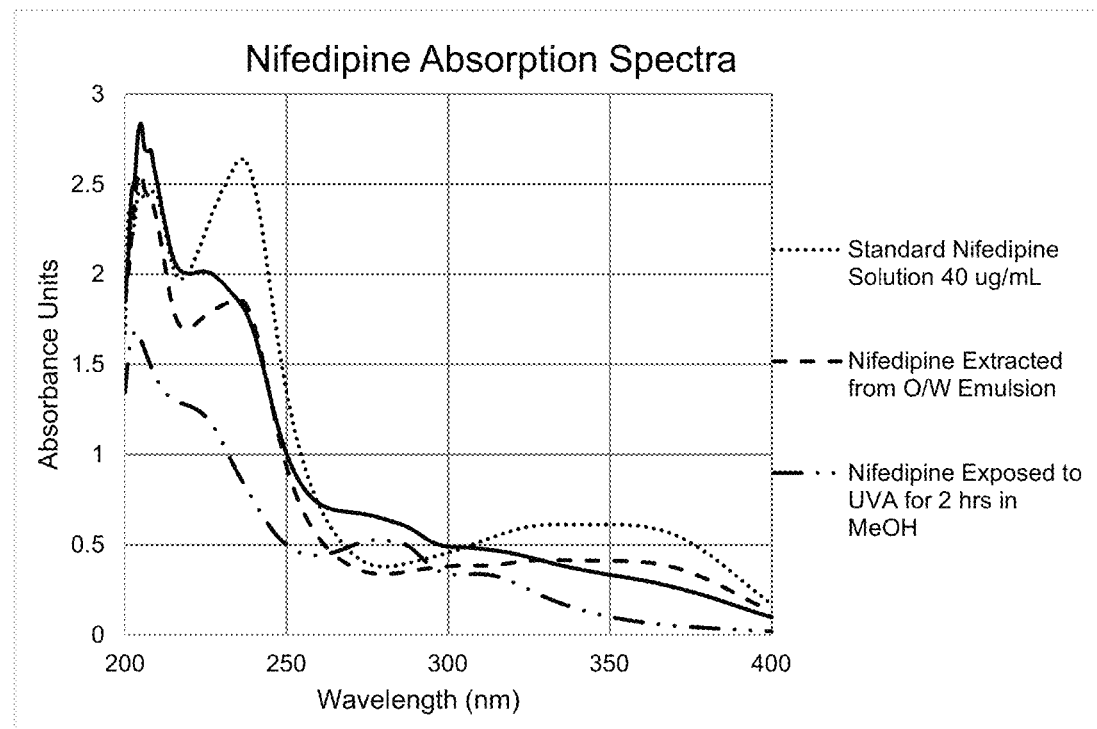

UV spectroscopy clearly showed the change in the absorption spectrum of nifedipine after exposure to UVA light (FIG. 1). A solution of nifedipine in methanol showed a peak absorbance at 348 nm. A methanol extract of nifedipine cream [2% (w/w) as O/W emulsion] showed a similar spectrum. However, after 2 hr of intense UVA exposure (750 µW/cm$^2$) this peak decreased and a new peak formed at 280 nm. The appearance of the peak at 280 nm corresponds to the peak absorbance of the nifedipine photodegradation product, dehydronitrosonifedipine. While not wishing to be limited by theory, the 280/348 nm ratio of absorption intensity suggests that the O/W emulsion imparts some, albeit incomplete, photoprotection of the nifedipine to UVA light. Further analysis of the photodegradation product was investigated by mass spectrometry as discussed hereinbelow.

Figure 2:
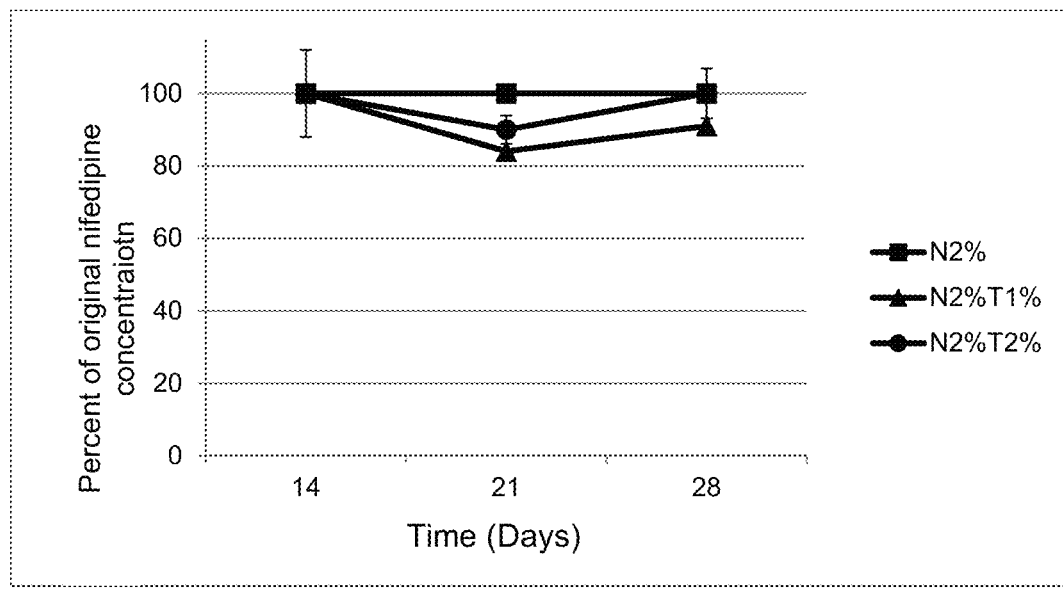
Figure 3:
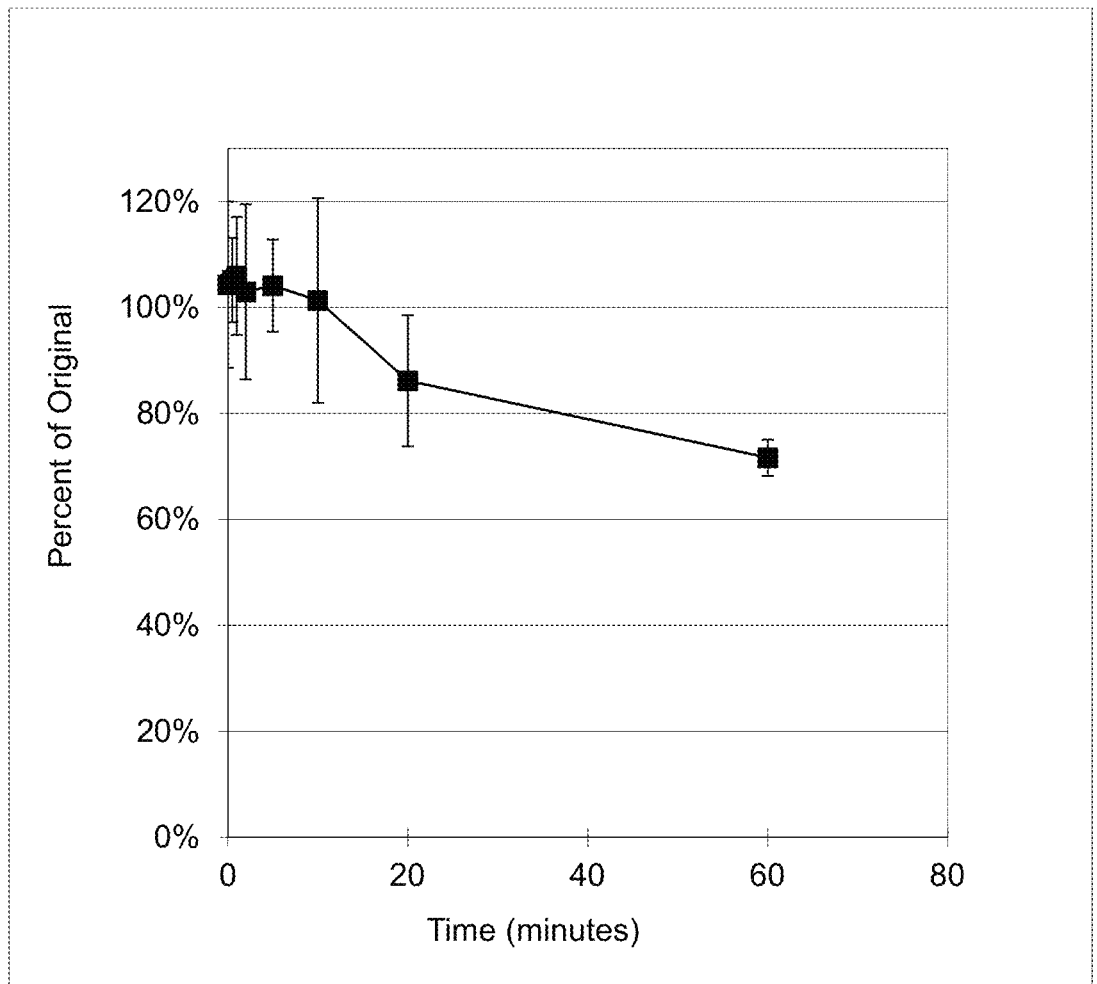
FIG. 3 is a plot showing percent of original concentration of nifedipine as a function of time (minutes) for nifedipine (2% w/w) cream according to a comparative example of the present application exposed as a thin film to ambient light over 1 hr. Data represent mean±SD (n=3).
Figure 4:
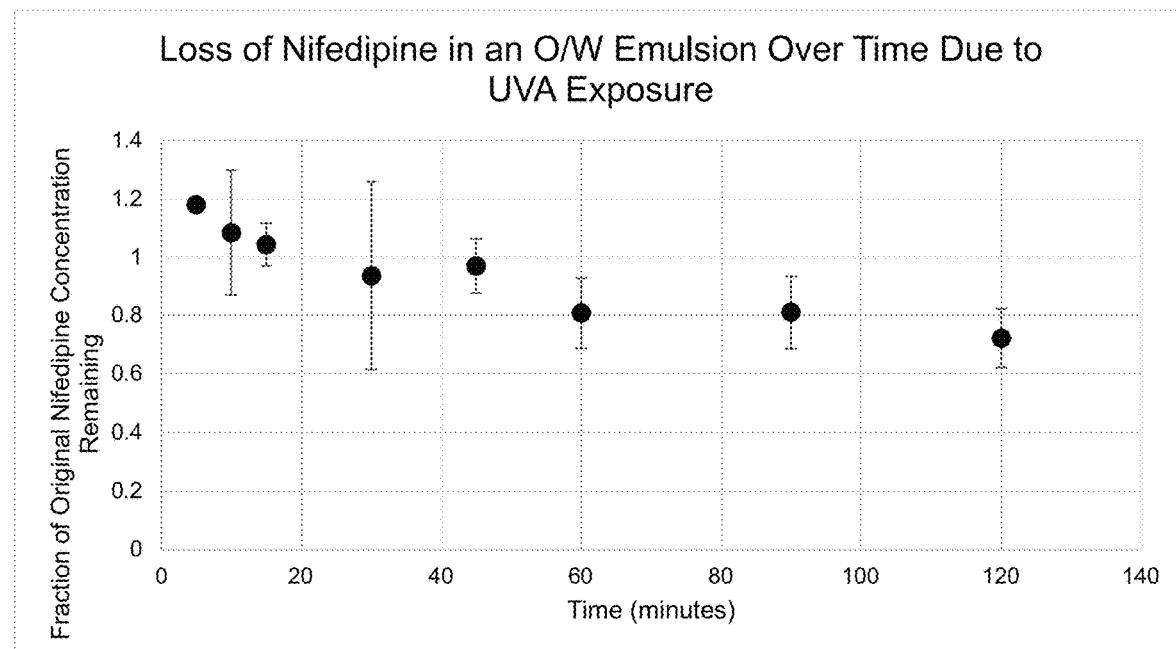
FIG. 4 is a plot showing percent of original concentration of nifedipine as a function of time (minutes) for nifedipine (2% w/w) cream according to a comparative example of the present application exposed as a thin film to UVA light (750 μW/cm$^2$) over 2 hr. Data represent mean±SD (n=3).
Figure 5:
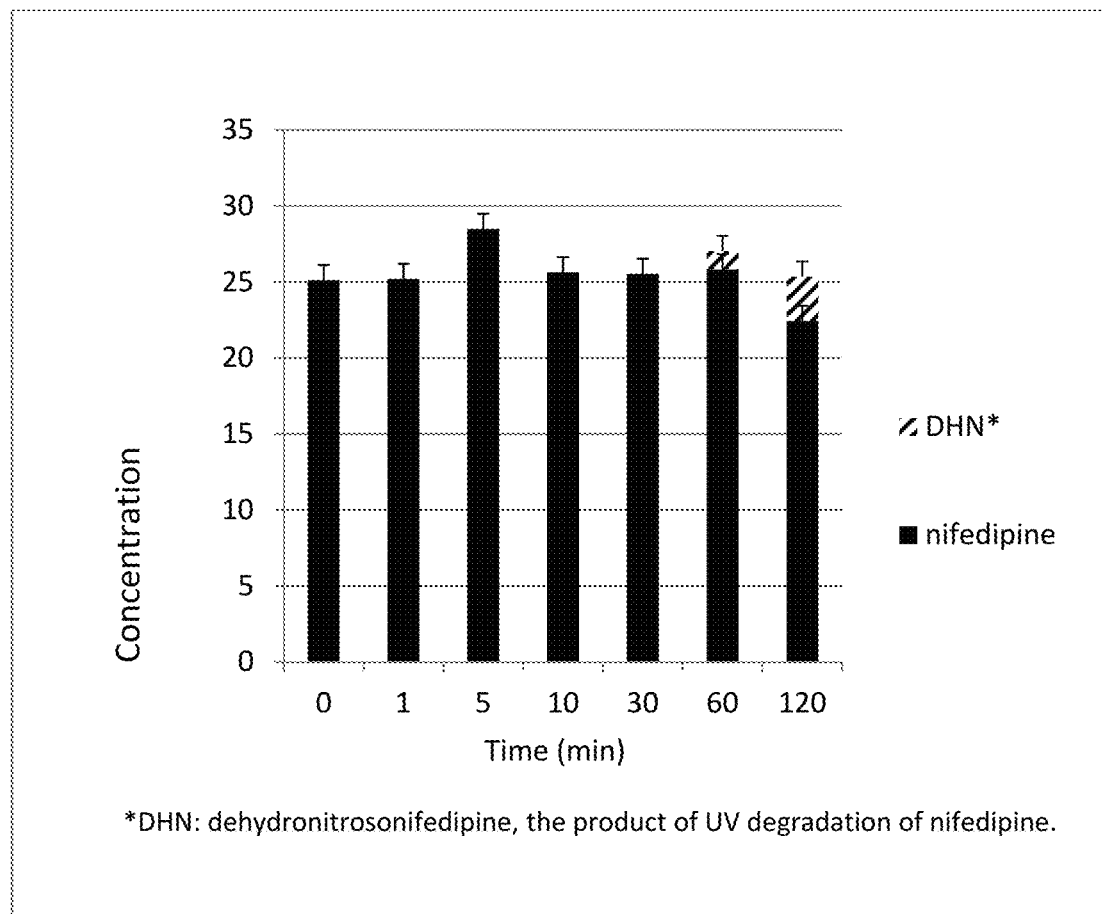
FIG. 5 is a plot showing that the reduction in nifedipine concentration measured by high performance liquid chromatography (HPLC) over time (minutes) following ambient light exposure corresponds with appearance of the photodegradation product dehydronitrosonifedipine (DHN). Data represent mean±SD (n=3).

Nifedipine stability in the cream prepared as 1% or 2% w/w nifedipine with or without Transcutol HP (1% or 2% w/w) was determined under light-protected conditions at 23° C. and found to be maintained at >95% of original concentration for at least 1 month (FIG. 2). However, upon exposure as a thin film to indoor fluorescent room light nifedipine concentration began to decline at 20 min, reduced to 75% of its original concentration by 1 hr. (FIG. 3) After exposure to UVA light at 750 µW/cm$^2$, the nifedipine in the cream was reduced to 70% of its original concentration after two hours (FIG. 4). The major degradation product, dehydronitrosonifedipine (DHN) was quantified by HPLC and appeared by 1 h (FIG. 5).

Figure 6:
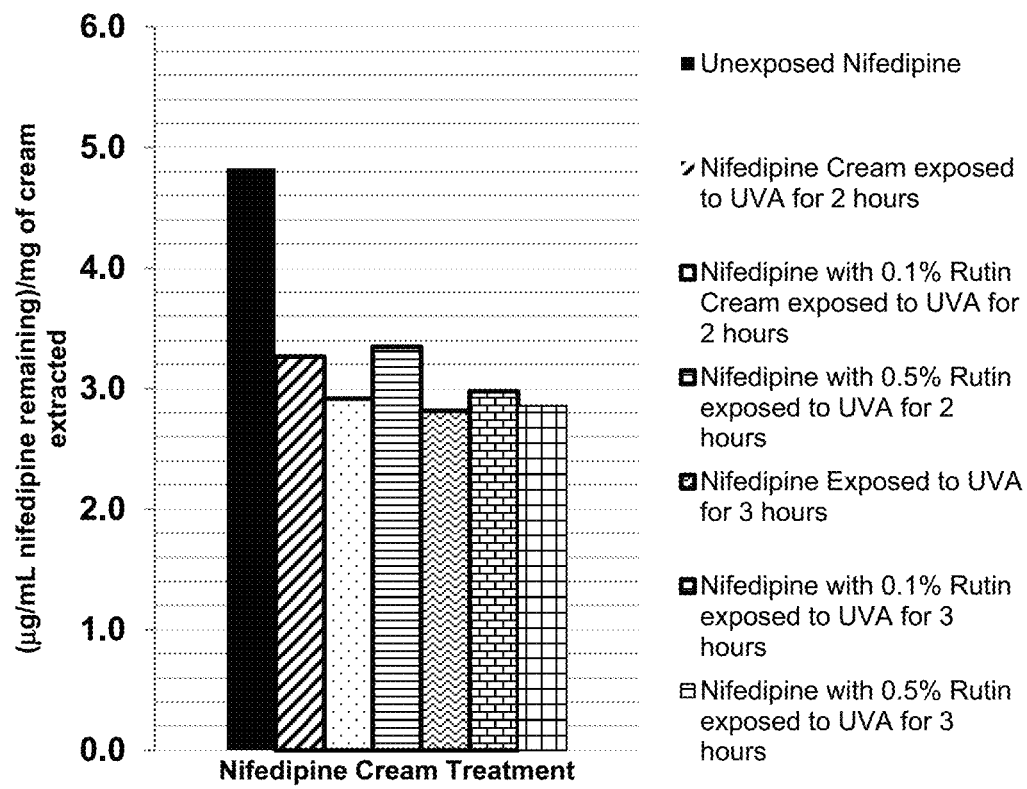
FIG. 6 is a plot showing the concentration (μg/mL) nifedipine remaining/mg of cream extracted for creams with nifedipine and rutin [0.1% or 0.5% (w/w)] in comparison to nifedipine creams without rutin according to comparative examples of the present application after UVA exposure (750 μW/cm$^2$) over a period of 2 or 3 h. Data represent mean±SD (n=3).
Figure 7:
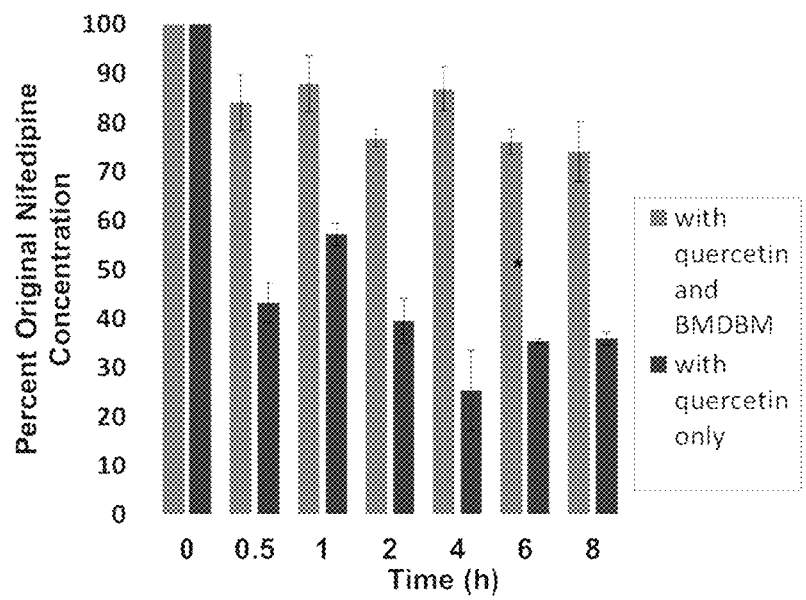
FIG. 7 is a plot showing the percent original nifedipine concentration as a function of time (hours) for creams with quercetin [0.5% (w/w)] and with quercetin [0.5% (w/w)] and BMDBM [3% (w/w)] incorporated into a nifedipine 2% (w/w) cream as a photostabilizer according to examples of the topical formulations of (492 μW/cm$^2$) Data represent mean±SD (n=3).

To investigate the use of select photostabilizers on light stability, rutin, BMDBM and/or quercetin were incorporated at varying concentrations up to 3% w/w in the emulsion as UVA filters. Incorporation of rutin at concentrations of 0.5-3% (w/w) did not significantly reduce UVA-induced degradation of nifedipine over 3 hrs when a 20 mg thin film was exposed (FIG. 6). However, the chemically related compound quercetin (FIG. 7) in combination with BMDBM increased the stability of nifedipine to UVA light. (FIG. 8) Quercetin alone at 0.5% (w/w) was moderately effective on its own to protect nifedipine from degradation. BMDBM alone was moderately effective, (FIG. 8) however the combination of quercetin and BMDBM was very effective, with 80% of the original nifedipine concentration maintained after 8 h of UVA exposure at 450 µW/cm$^2$ (FIG. 7) and >55% at 750 µW/cm$^2$ (FIG. 8).

To study whether these additional excipients might reduce the physical stability of the emulsion by affecting viscosity or emulsion droplet formation, the creaming rate and extent were assessed in a temperature-controlled photocentrifuge whereby an increased transmission to light indicates phase separation, which is then calculated as an instability index (FIG. 9, showing differences between emulsion stability depending on presence of specific photostabilizers). If an excipient caused a significant change in viscosity, for example, phase separation would occur more quickly and adversely affect emulsion stability on storage. This information can, for example, drive the decision to choose between two excipients that are otherwise performing similarly. The incorporation of quercetin or BMDBM reduced the instability of the nifedipine emulsion, while not wishing to be limited by theory, by altering the emulsion viscosity.

Mass spectrometry was used to determine which nifedipine degradation products occur following UV exposure when one or more of the photostabilizers (rutin, quercetin, BMDBM) was present. Dehydronifedipine and dehydronitrosonifedipine were found in UVA-exposed creams, with no alternative degradation pathways identified in the presence of these photostabilizers based on appearance of m/z consistent with their expected profiles. FIG. 10 shows an example mass spectrum Q1 scan of nifedipine [2% (w/w)] containing rutin [0.5% (w/w)] with 6 hrs of UVA exposure. Scheme 1 shows structures of compounds related to the photodegradation of nifedipine[37].

Scheme 1

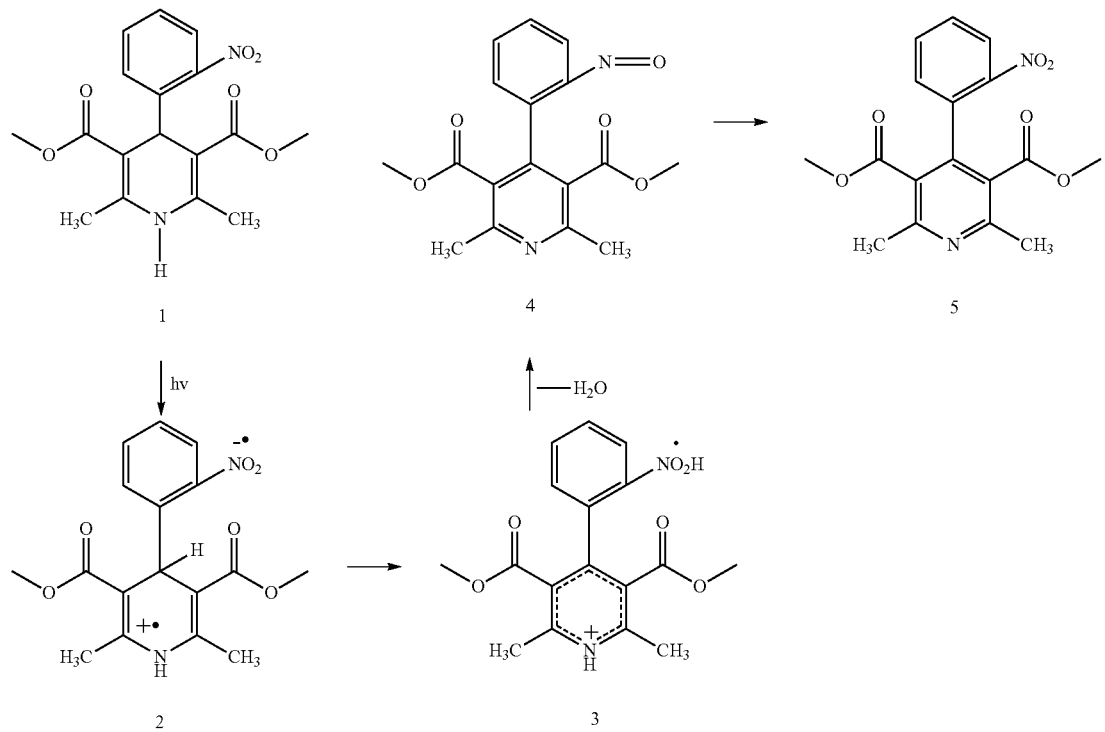

In Scheme 1, nifedipine (MW=344.3 g/mol) (1) undergoes photoconversion to the corresponding dehydronitrosonifedipine (4-(2-nitrosophenyl)-2,6-dimethyl-3,5-dimethoxycarbonypyridine) (4). This process is independent of irradiation wavelength and insensitive to the presence of oxygen. This step involves photoexcitation of the dihydropyridine moiety in nifedipine corresponding to the lowest singlet excited state. This is followed by rapid intramolecular electron transfer from the excited dihydropyridine moiety to the nitrobenzene-accepting group to give the biradical intermediate (2). The formation of (3) is compatible with proton transfer between the two oppositely charged moieties in (2) to generate the aromatic species. Loss of water leads to the major photodegradation product dehydronitrosonifedipine (MW=328.32 g/mol) (4). Further thermal or photoreaction of dehydronitrosonifedipine gives the dehydronifedipine product dimethyl 2,6-dimethyl-4-(2-nitrophenyl)-3,5-pyridinedicarboxylate (5).

Nifedipine (labelled as 1 in Scheme 1 and the sodium adduct thereof labelled as 1a in FIG. 10) and its photodegradation product, dehydronitrosonifedipine (labelled as 4 in both Scheme 1 and FIG. 10, and the sodium adduct thereof labelled as 4a in FIG. 10) are evident. In particular, the parent compound nifedipine is observed in the form of a sodium adduct at an m/z of 369.3 (4a) in FIG. 10 and the appearance of m/z=329 is consistent with dehydronitrosonifedipine (4) formation which is also observed as the sodium adduct (4a) m/z=351. For m/z=157.3 (*) and 115.3 (**), these represent daughter ions of the parent nifedipine compound. The nifedipine was not protected from photodegradation by rutin, therefore the dehydronitrosonifedipine appears.

Further investigation of the various photoprotectants rutin, quercetin and BMDBM indicated no unexpected daughter ion formation on mass spectrometry to indicate any alternate degradation pathways in the presence of the antioxidants quercetin or rutin, or with BMDBM.

FIG. 11 is a mass spectrum that shows the relative lack of appearance of photodegradation product in nifedipine 2% cream containing 0.5% quercetin [0.5% (w/w) and BMDBM (3% (w/w)] that was exposed to UVA×6 hr at 450 µW/cm². The parent nifedipine compound is again shown (1a) as the sodium adduct (m/z=369.4) and BMDBM, m/z=333.3 (2) is also observed. However, there is less evidence of dehydronitrosonifedipine (m/z=329 and as sodium adduct 351) than in FIG. 10. m/z=291 (3) represents a daughter ion from nifedipine. The peak at m/z=329 is apparent in the nifedipine/rutin cream (FIG. 10) but less so in the nifedipine/quercetin/BMDBM cream (FIG. 11) after 6 hr of exposure. This is consistent with the HPLC analysis of nifedipine and dehydronitrosonifedipine concentration versus exposure time discussed herein above.

Experiments to assess the diffusion of nifedipine through model skin membranes (Strat-M) were performed at 32° C. using a static vertical diffusion apparatus (Franz cells) indicated transmembrane transfer continuously over 6 hrs with a suggestion of differences between formulations containing photostabilizers quercetin and/or BMDBM. Diffusion of nifedipine from the emulsion to the receptor compartment (made up of saline and 20% ethanol to permit drug solubility) was determined.[38] There were differences in the cumulative amount of drug transferred from the nifedipine emulsions when the photostabilizer component was varied (FIG. 12), but the drug did diffuse for all samples.

III. Discussion

Incorporation of nifedipine into an O/W emulsion affords some protection from UVA-induced photodegradation. However, following 2 h exposure, only 72%+/−7.9% of the nifedipine remains.

Rutin, although it is an antioxidant and is highly absorbent in the UVA range, was found to be ineffective as a photoprotectant for nifedipine in this O/W emulsion preparation at concentrations up to 2% (w/w). No significant difference in nifedipine concentration was found between preparations with and without rutin after 2 h UVA exposure.

When quercetin (0.5% w/w) was incorporated into the nifedipine cream, photostability was improved after UVA exposure. In combination with BMDBM, a further improvement to at least 75% of the original concentration even after 8 h of UVA exposure was observed.

It is desirable to minimize phostabilizer degradation under broad spectrum UV light [UVA (95% of UV light reaching Earth, 315-400 nm) plus UVB (280-315 nm)]. The present studies have shown that the combination of BMDBM and quercetin is effective in maintaining nifedipine concentration under UVA light exposure over the typical time period in which the nifedipine would be exposed to such light during use. While not wishing to be limited by theory, quercetin's antioxidant properties may stabilize BMDBM in such a formulation.[39]

Analysis by mass spectrometry aided the understanding of the degradation profile of nifedipine in UVA-exposed o/w emulsions in the presence of rutin, quercetin and/or BMDBM incorporated into the nifedipine cream.

This O/W emulsion formulation of nifedipine does permit diffusion of nifedipine from the emulsion across model skin membranes, which may be useful for its applications, for example, for the topical treatment of Raynaud phenomenon and chilblains where skin penetration is necessary for efficacy. Diffusion of nifedipine across skin may also be useful in wound healing applications but because the site of action is the dermis, a topical nifedipine formulation may additionally have effects on the surface of the skin.

These topical nifedipine formulations containing quercetin and/or BMDBM may, for example, be useful for reducing tissue damage in patients with scleroderma, rheumatoid arthritis, systemic lupus erythematosus and Sjögen's syndrome, optionally as a part of combination pharmacological therapy for RP and/or for those who have outdoor occupations. Furthermore, such topical nifedipine formulations, may, for example, be used for wound healing[40], peripheral vascular insufficiency-related conditions, and/or in diabetic ulcer or scleroderma-associated ulcer treatment.[41]

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

[1] Garner, R., et al., *Prevalence, risk factors and associations of primary Raynaud's phenomenon: systematic review and meta-analysis of observational studies*. BMJ Open, 2015. 5(3): p. e006389.

[2] Prete, M., et al., *Raynaud's phenomenon: from molecular pathogenesis to therapy*. Autoimmun Rev, 2014. 13(6): p. 655-67.

[3] Scleroderma Association of Saskatchewan, Scleroderma: *Disease Definition*. 2017.

[4] (a) Pope, J. E., *The diagnosis and treatment of Raynaud's phenomenon: a practical approach*. Drugs, 2007. 67(4): p. 517-25; (b) Kaul, A., et al., *Systemic lupus erythematosus*. Nature Reviews Disease Primers, 2016. 2: p. 16039.

[5] (a) Goundry, B., et al., *Diagnosis and management of Raynaud's phenomenon*. Bmj, 2012. 344: p. e289; (b) Valdovinos, S. T. and G. J. Landry, *Raynaud syndrome*. Tech Vasc Interv Radiol, 2014. 17(4): p. 241-6; (c) Barrett, M. E., et al., *Raynaud phenomenon of the nipple in breastfeeding mothers: an underdiagnosed cause of nipple pain*. JAMA Dermatol, 2013. 149(3): p. 300-6.

[6] (a) Flavahan, N. A., *A vascular mechanistic approach to understanding Raynaud phenomenon*. Nat Rev Rheumatol, 2015. 11(3): p. 146-58; (b) Baumhakel, M. and M. Bohm, *Recent achievements in the management of Raynaud's phenomenon*. Vasc Health Risk Manag, 2010. 6: p. 207-14.

[7] Plissonneau Duquene, P., et al., *Cold climate could be an etiologic factor involved in Raynaud's phenomenon physiopathology. Epidemiological investigation from 954 consultations in general practic*. Int Angiol, 2015. 34(5): p. 467-74.

[8] Hughes, M., et al., *Prediction and impact of attacks of Raynaud's phenomenon, as judged by patient perception*. Rheumatology (Oxford), 2015. 54(8): p. 1443-7.

[9] Merkel, P. A., et al., *Measuring disease activity and functional status in patients with scleroderma and Raynaud's phenomenon*. Arthritis Rheum, 2002. 46(9): p. 2410-20.

[10] (a) Ennis, H., et al., *Calcium channel blockers for primary Raynaud's phenomenon*. Cochrane Database Syst Rev, 2014. 1: p. Cd002069; (b) Landry, G. J., *Current medical and surgical management of Raynaud's syndrome*. J Vasc Surg, 2013. 57(6): p. 1710-6; (c) Nguyen, H. and A. M. Amanullah, *Therapeutic potentials of phosphodiesterase-5 inhibitors in cardiovascular disease*. Rev Cardiovasc Med, 2014. 15(2): p. 158-67; (d) Stewart, M. and J. R. Morling, *Oral vasodilators for primary Raynaud's phenomenon*. Cochrane Database Syst Rev, 2012. 7: p. Cd006687; (e) Garcia de la Pena Lefebvre, P., et al., *Efficacy of Raynaud's phenomenon and digital ulcer pharmacological treatment in systemic sclerosis patients: a systematic literature review*. Rheumatol Int, 2015. 35(9): p. 1447-59.

[11] Ennis, H., et al., *Calcium channel blockers for primary Raynaud's phenomenon*. Cochrane Database Syst Rev, 2016. 2: p. Cd002069.

[12] (a) Negrini, S., et al., *Efficacy of cilostazol for the treatment of Raynaud's phenomenon in systemic sclerosis patients*. Clin Exp Med, 2015; (b) Pope, J., et al., *Iloprost and cisaprost for Raynaud's phenomenon in progressive systemic sclerosis*. Cochrane Database Syst Rev, 2000(2): p. Cd000953.

[13] (a) Iorio, M. L., D. L. Masden, and J. P. Higgins, *Botulinum toxin A treatment of Raynaud's phenomenon: a review*. Semin Arthritis Rheum, 2012. 41(4): p. 599-603; (b) Linnemann, B. and M. Erbe, *Raynaud's phenomenon and digital ischaemia*—pharmacologic approach and alternative treatment options. Vasa, 2016. 45(3): p. 201-12.

[14] Merritt, W. H., *Role and rationale for extended periarterial sympathectomy in the management of severe Raynaud syndrome: techniques and results*. Hand Clin, 2015. 31(1): p. 101-20.

[15] Landry, G. J., *Current medical and surgical management of Raynaud's syndrome*. J Vasc Surg, 2013. 57(6): p. 1710-6.

[16] Ennis, H., et al., *Calcium channel blockers for primary Raynaud's phenomenon*. Cochrane Database Syst Rev, 2014. 1: p. Cd002069.

[17] Stewart, M. and J. R. Morling, *Oral vasodilators for primary Raynaud's phenomenon*. Cochrane Database Syst Rev, 2012. 7: p. Cd006687.

[18] Chung, L., et al., *MQX-503, a novel formulation of nitroglycerin, improves the severity of Raynaud's phenomenon: a randomized, controlled trial*. Arthritis Rheum, 2009. 60(3): p. 870-7.

[19] Pope, J. E., *The diagnosis and treatment of Raynaud's phenomenon: a practical approach*. Drugs, 2007. 67(4): p. 517-25.

[20] Teh, L. S., et al., *Sustained-release transdermal glyceryl trinitrate patches as a treatment for primary and secondary Raynaud's phenomenon*. Br J Rheumatol, 1995. 34(7): p. 636-41.

[21] Daiber, A. and T. Munzel, *Organic Nitrate Therapy, Nitrate Tolerance, and Nitrate-Induced Endothelial Dysfunction: Emphasis on Redox Biology and Oxidative Stress*. Antioxid Redox Signal, 2015. 23(11): p. 899-942.

[22] Garcia-Carrasco, M., et al., *Treatment of Raynaud's phenomenon*. Autoimmunity Reviews, 2008. 8(1): p. 62-68.

[23] McClusky S, B., G, *Nifedipine in Compounded Oral and Topical Preparations*. International Journal of Pharmaceutical Compounding, 2013. 15(2): p. 166-169.

[24] (a) Lane, M. E., *Skin penetration enhancers*. Int J Pharm, 2013. 447(1-2): p. 12-21; (b) Ita, K. B., *Chemical Penetration Enhancers for Transdermal Drug Delivery—Success and Challenges*. Curr Drug Deliv, 2015. 12(6): p. 645-51.

[25] (a) Sullivan, D. W., Jr., S. C. Gad, and M. Julien, *A review of the nonclinical safety of Transcutol(R), a highly purified form of diethylene glycol monoethyl ether (DEGEE) used as a pharmaceutical excipient*. Food Chem Toxicol, 2014. 72: p. 40-50; (b) Osborne, D. W., *Diethylene glycol monoethyl ether: an emerging solvent in topical dermatology products*. J Cosmet Dermatol, 2011. 10(4): p. 324-9.

[26] Baertschi, S. W., et al., *Implications of In-Use Photostability: Proposed Guidance for Photostability Testing and Labeling to Support the Administration of Photosensitive Pharmaceutical Products, Part 2: Topical Drug Product*. Journal of Pharmaceutical Sciences, 2015. 104(9): p. 2688-2701.

[27] Tonnesen, H. H., *Photostability of drugs and drug formulations*. 2004: CRC Press.

[28] Cosa, G., *Photodegradation and photosensitization in pharmaceutical products: Assessing drug phototoxicity*, in *Pure and Applied Chemistry*. 2004. p. 263.

[29] (a) Hayase, N., et al., *Newly discovered photodegradation products of nifedipine in hospital prescriptions*. J Pharm Sci, 1994. 83(4): p. 532-8; (b) Aman, W. and K. Thoma, *Particular features of photolabile substances in tablets*. Pharmazie, 2003. 58(9): p. 645-50; (c) Groener, H., *Nitro group photoreduction of 4-(2-nitrophenyl)—and 4-(3-nitrophenyl)-1,4-dihydropyridines*. Chemical Physics, 2010. 373(3): p. 153-158; (d) Grooff, D., et al., *Photostability of crystalline versus amorphous nifedipine and nimodipine*. J Pharm Sci, 2013. 102(6): p. 1883-94.

[30] (a) Adkins, J. C. and D. Faulds, *Amprenavir*. Drugs, 1998. 55(6): p. 837-42; discussion 843-4; (b) Chaiprasongsuk, A., et al., *Photoprotection by dietary phenolics against melanogenesis induced by UVA through Nrf2-dependent antioxidant responses*. Redox Biol, 2016. 8: p. 79-90; (c) Choquenet, B., et al., *Quercetin and rutin as potential sunscreen agents: determination of efficacy by an in vitro method*. J Nat Prod, 2008. 71(6): p. 1117-8.

[31] (a) Kockler, J., et al., *Butyl methoxy dibenzoylmethane*. Profiles Drug Subst Excip Relat Methodol, 2013. 38: p. 87-111; (b) Kockler, J., et al., *Chapter Three—Butyl Methoxy Dibenzoylmethane*, in *Profiles of Drug Substances, Excipients and Related Methodology*, G. B. Harry, Editor. 2013, Academic Press. p. 87-111.

[32] (a) Gopalakrishnan, A., et al., *Quercetin accelerated cutaneous wound healing in rats by increasing levels of VEGF and TGF-beta1*. Indian J Exp Biol, 2016. 54(3): p. 187-95; (b) Hatahet, T., Morille, M., Hommoss, A., Devoisselle, J. M. Muller, R. H., Begu, S. (2016). "Quercetin topical application, from conventional dosage forms to nanodosage forms." Eur J Pharm Biopharm 108: 41-53.

[33] Grey J E, Harding K G, Enoch S. Venous and arterial leg ulcers. BMJ: British Medical Journal. 2006; 332(7537):347-350.

[34] (a) Baert, B., et al., *A new discriminative criterion for the development of Franz diffusion tests for transdermal pharmaceuticals*. J Pharm Pharm Sci, 2010. 13(2): p. 218-30; (b) Uchida, T., et al., *Prediction of skin permeation by chemical compounds using the artificial membrane, Strat-M™*. European Journal of Pharmaceutical Sciences, 2015. 67: p. 113-118; (c) Karadzovska, D. and J. E. Riviere, *Assessing vehicle effects on skin absorption using artificial membrane assays*. European Journal of Pharmaceutical Sciences, 2013. 50(5): p. 569-576.

[35] (a) Xu D, Aihemaiti Z, Cao Y, Teng C, Li. *Physicochemical stability, microrheological properties and microstructure of lutein emulsions stabilized by multilayer membranes consisting of whey protein isolate, flaxseed gum and chitosan*. Food Chemistry, 2016. 202: p. 156-164; (b) Ghosh, S, Pradhan M, Patel T, Haj-Shafiei S, Rousseau D *Long-term stability of crystal-stabilized water-in-oil emulsions*. J Colloid Interface Sci, 2015. 460: p. 247-257; (c) Cui, F., Yang M, Jiang Y, Cun D, Lin W, Fan Y, Kawashima Y. *Design of sustained-release nitrendipine microspheres having solid dispersion structure by quasi-emulsion solvent diffusion method*. Journal of Controlled Release, 2003. 91(3): p. 375-384.

[36] Streel B, Zimmer C, Sibenaler R, Ceccato A. *Simultaneous determination of nifedipine and dehydronifedipine in human plasma by liquid chromatography-tandem mass spectrometry*. J Chromatogr B Biomed Sci Appl. 1998 720(1-2): 119-28.

[37] (a) Fasani E, Dondi D, Ricci A, Albini A. (2006) Photochemistry of 4-(2-Nitrophenyl)-1,4-Dihydropyridines. Evidence for Electron Transfer and Formation of an Intermediate. Photochem Photobiol 82 (1), 225-230; (b) Görner H. (2010) Nitro group photoreduction of 4-(2-nitrophenyl)- and 4-(3-nitrophenyl)-1,4-dihydropyridines, Chem Phys, 373 (3), 153-158.

[38] Naik P, Shah S M, Heaney J, Hanson R, and Nagarsenker M S. (2016) *Influence of Test Parameters on Release Rate of Hydrocortisone from Cream: Study Using Vertical Diffusion Cell*. Dissolution Technologies August 2016. dx.doi.org/1 0. 14227/DT230316 P14.

[39] (a) Afonso, S., et al., *Photodegradation of avobenzone: stabilization effect of antioxidants*. J Photochem Photobiol B, 2014. 140: p. 36-40; (b) Gaspar, L. R. and P. M. Campos, *Photostability and efficacy studies of topical formulations containing UV-filters combination and vitamins A, C and E*. Int J Pharm, 2007. 343(1-2): p. 181-9.

[40] (a) Golfam, F., et al., *The effect of topical nifedipine in treatment of chronic anal fissure*. Acta Med Iran, 2010. 48(5): p. 295-9; (b) Agrawal, V., G. Kaushal, and R. Gupta, *Randomized controlled pilot trial of nifedipine as oral therapy vs. topical application in the treatment of fissure-in-ano*. Am J Surg, 2013. 206(5): p. 748-51; (c) Ashkani-Esfahani, S., et al., *Verapamil, a Calcium-Channel Blocker, Improves the Wound Healing Process in Rats with Excisional Full-Thickness Skin Wounds Based on Stereological Parameters*. Adv Skin Wound Care, 2016. 29(8): p. 271-4; (d) Pai, D. R. and S. S. Madan, *Techniques in Chronic Wound Management: Review of the Literature and Recent Concept*. Journal of Novel Physiotherapies, 2013. 3: p. 2; (e) Torsiello, M. J. and M. Kopacki, *Transdermal nifedipine for wound healing: case reports*. International Journal of Pharmaceutical Compounding, 2000. 4(5): p. 356-358; (f) Golfam, F., et al., *Comparison of topical nifedipine with oral nifedipine for treatment of anal fissure: a randomized controlled trial*. Iran Red Crescent Med J, 2014. 16(8): p. e13592; (g) Bhaskar, H. N., S. L. Udupa, and A. L. Udupa, *Effect of nifedipine and amlodipine on dead space wound healing in rats*. Indian J Exp Biol, 2005. 43(3): p. 294-6; (h) Bhaskar, K., et al., *Development of nitrendipine controlled release formulations based on SLN and NLC for topical delivery: in vitro and ex vivo characterization*. Drug Dev Ind Pharm, 2008. 34(7): p. 719-25; (i) Bagheri, M., et al., *Azelnidipine, a new calcium channel blocker, —promotes skin wound healing in diabetic rats*. J Surg Res, 2011. 169(1): p. e101-7; (j) Yang, S. Y., et al., *A Comparison of Gene Expression of Decorin and MMP13 in Hypertrophic Scars Treated With Calcium Channel Blocker, Steroid, and Interferon: A Human-Scar-Carrying Animal Model Study*. Dermatol Surg, 2017. 43 Suppl 1: p. S37-s46; (k) Vedakumari W S, Ayaz N, Karthick A S, Senthil R, Sastry T P. (2017) *Quercetin impregnated chitosan-fibrin composite scaffolds as potential wound dressing materials—Fabrication, characterization and in vivo analysis*. Eur J Pharm Sci. 2017 Jan. 15; 97:106-112. doi: 10.1016/j.ejps.2016.11.012. Epub 2016 Nov. 15; (l) Hatahet T, Morille M, Hommoss A, Devoisselle J M, Müller RH, Begu S (2016) *Quercetin topical application, from conventional dosage forms to nanodosage forms*. Eur J Pharm Biopharm. 2016 November; 108:41-53. doi: 10.1016/j.ejpb.2016.08.011. Epub 2016 Aug. 24; (m) Woo T Y, Wong R C, Campbell J P, Goldfarb M T, Voorhees J J, Callen J P. (1984) *Nifedipine in scleroderma ulcerations*. Int J Dermatol. 23(10):678-80; (n) Gopalakrishnan A, Ram M, Kumawat S, Tandan S, Kumar D (2016) *Quercetin accelerated cutaneous wound healing in rats by increasing levels of VEGF and TGF-β1*. Indian J Exp Biol. 2016 March; 54(3):187-95; (o) Seo S H, Lee S H, Cha P H, Kim M Y, Min do S, Choi K Y (2016) *Polygonum aviculare L. and its active compounds, quercitrin hydrate, caffeic acid, and rutin, activate the Wnt/β-catenin pathway and induce cutaneous wound healing*. Phytother Res. 2016 May; 30(5):848-54. doi: 10.1002/ptr.5593. Epub 2016 Mar. 1.

[41] (a) Grant, S. M. and K. L. Goa, *Iloprost. A review of its pharmacodynamic and pharmacokinetic properties, and therapeutic potential in peripheral vascular disease, myocardial ischaemia and extracorporeal circulation procedures*. Drugs, 1992. 43(6): p. 889-924; (b) Hotkar, M. S., et al., *Preliminary investigation of topical nitroglycerin formulations containing natural wound healing agent in diabetes-induced foot ulcer*. Int Wound J, 2015. 12(2): p. 210-7; (c) O'Meara, S., et al., *Systematic reviews of wound care management: (3) antimicrobial agents for chronic wounds; (4) diabetic foot ulceration*. Health Technol Assess, 2000. 4(21): p. 1-237; (d) Wu, S. C., et al., *Foot ulcers in the diabetic patient, prevention and treatment*. Vasc Health Risk Manag, 2007. 3(1): p. 65-76; (e) Singh, N., D. G. Armstrong, and B. A. Lipsky, *Preventing foot ulcers in patients with diabetes*. Jama, 2005. 293(2): p. 217-28; (f) Information, C.I.f.H., *Compromised wounds in Canada*. 2013; (g) Tom, W., *Case Report: Wound Care of a Diabetic Foot Ulcer*. International Journal of Pharmaceutical Compounding, 2004. July: p. 265; (h) Grossman J A, Barrall D T, Dennison A, Lally E V. (1988) *Successful combined medical and surgical treatment of a lower extremity sclerodermal ulcer*. Ann Plast Surg. 20(6):582-585; (i) Castangia I, Nácher A, Caddeo C, Valenti D, Fadda A M, Diez-Sales O, Ruiz-Sauri A, Manconi M. (2014) *Fabrication of quercetin and curcumin bionanovesicles for the prevention and rapid regeneration of full-thickness skin defects on mice*. Acta Biomater. 10(3):1292-300. doi: 10.1016/j.actbio.2013.11.005. Epub 2013 Nov. 15.

The invention claimed is:

1. A topical formulation in the form of an oil-in-water emulsion comprising nifedipine and a photostabilizing effective amount of a combination of quercetin and butyl methoxydibenzoylmethane (BMDBM), wherein the quercetin is present in the topical formulation in an amount of from about 0.1% w/w to about 3% w/w and the BMDBM is present in the topical formulation in an amount of from about 0.1% w/w to about 4% w/w.

2. The topical formulation of claim 1, further comprising one or more of: penetration enhancer, emulsifier, emulsion stabilizer, moisturizer, solvent, emollient, thickener, humectant and surfactant.

3. The topical formulation of claim 1, further comprising glyceryl monostearate, stearic acid, liquid paraffin, petrolatum and diethylene glycol monoethyl ether.

4. The topical formulation of claim 3, wherein
the glyceryl monostearate is present in the topical formulation in an amount of from about 5% w/w to about 10% w/w;
the stearic acid is present in the topical formulation in an amount of from about 5% w/w to about 15% w/w;
the liquid paraffin is present in the topical formulation in an amount of from about 5% w/w to about 15% w/w;
the petrolatum is present in the topical formulation in an amount of from about 5% w/w to about 15% w/w; and
the diethylene glycol monoethyl ether is present in the topical formulation in an amount of from about 0.1% w/w to about 3% w/w,
all values for % w/w being based on the total weight of the topical formulation.

5. The topical formulation of claim 1, further comprising water, glycerin and an anionic surfactant.

6. The topical formulation of claim 5, wherein
the water is present in the topical formulation in an amount of from about 45% w/w to about 60% w/w;
the glycerin is present in the topical formulation in an amount of from about 10% w/w to about 20% w/w; and
the anionic surfactant is sodium laurel sulfate present in the topical formulation in an amount of from about 0.1% w/w to about 2% w/w,
all values for % w/w being based on the total weight of the topical formulation.

7. The topical formulation of claim 1, wherein the nifedipine is present in the topical formulation in an amount of from about 0.1% w/w to about 5% w/w, based on the total weight of the topical formulation.

8. The topical formulation of claim 7, wherein the nifedipine is present in an amount of about 2% w/w, based on the total weight of the topical formulation.

9. The topical formulation of claim 1, wherein the quercetin is present in an amount of about 0.5% w/w, based on the total weight of the topical formulation.

10. The topical formulation of claim 1, wherein the BMDBM is present in an amount of about 3% w/w, based on the total weight of the topical formulation.

11. The topical formulation of claim 1, wherein about 80% w/w of the nifedipine in the topical formulation is present after exposing a thin film of the topical formulation to ultraviolet A (UVA) radiation at a flux of about 492 $\mu W/cm^2$ for about 8 hours.

12. The topical formulation of claim 1, in the form of a cream.

13. The topical formulation of claim 1, wherein the topical formulation is formulated for transdermal delivery of the nifedipine to the subject.

14. A method for treating a disease, disorder or condition that benefits from topical administration of nifedipine, the method comprising topically administering, to a subject in a need thereof, an effective amount of a topical formulation in the form of an oil-in-water emulsion comprising nifedipine and a photostabilizing effective amount of a combination of quercetin and butyl methoxydibenzoylmethane (BMDBM) as defined in claim 1.

15. The method of claim 14, wherein the disease, disorder or condition that benefits from topical administration of nifedipine is Raynaud's phenomenon.

16. The method of claim 14, wherein the disease, disorder or condition that benefits from topical administration of nifedipine is chilblains.

17. The method of claim 14, wherein the disease, disorder or condition that benefits from topical administration of nifedipine is a wound.

18. The method of claim 17, wherein the administration of the topical formulation reduces scarring in an incisional wound.

19. The method of claim 17, wherein the wound is a diabetic ulcer, a scleroderma-associated ulcer, a pressure sore or an anal fissure.

20. The method of claim 14, wherein the disease, disorder or condition that benefits from topical administration of nifedipine is a condition related to peripheral vascular insufficiency.

* * * * *